(12) United States Patent
Anderson et al.

(10) Patent No.: US 11,850,043 B2
(45) Date of Patent: Dec. 26, 2023

(54) SYSTEMS, DEVICES, AND METHODS FOR DETERMINING HEARING ABILITY AND TREATING HEARING LOSS

(71) Applicants: Dean Robert Gary Anderson, Orem, UT (US); Dean Gregory Anderson, Vernal, UT (US)

(72) Inventors: Dean Robert Gary Anderson, Orem, UT (US); Dean Gregory Anderson, Vernal, UT (US)

( * ) Notice: Subject to any disclaimer, the term of this patent is extended or adjusted under 35 U.S.C. 154(b) by 120 days.

(21) Appl. No.: 17/362,878

(22) Filed: Jun. 29, 2021

(65) Prior Publication Data

US 2021/0393170 A1    Dec. 23, 2021

Related U.S. Application Data

(62) Division of application No. 15/947,759, filed on Apr. 6, 2018, now Pat. No. 11,045,118.

(60) Provisional application No. 62/482,645, filed on Apr. 6, 2017.

(51) Int. Cl.
| | |
|---|---|
| *A61B 5/12* | (2006.01) |
| *G10K 15/02* | (2006.01) |
| *G06F 3/16* | (2006.01) |
| *A61B 5/00* | (2006.01) |
| *H04R 25/00* | (2006.01) |

(52) U.S. Cl.
CPC ............ *A61B 5/123* (2013.01); *A61B 5/4836* (2013.01); *G06F 3/165* (2013.01); *G10K 15/02* (2013.01); *H04R 25/603* (2019.05); *H04R 25/70* (2013.01); *H04R 2225/61* (2013.01)

(58) Field of Classification Search
CPC .. G10K 15/02; H04R 2225/61; H04R 25/603; H04R 25/70; H04B 7/04; H04B 7/0617; H04B 7/086; H04L 25/022; H04L 25/0222; H04L 25/0236; H04L 25/0248; H04L 25/03101; H04W 88/08
USPC ........ 381/60, 94.1–94.5, 71.1–71.6; 600/559
See application file for complete search history.

(56) References Cited

U.S. PATENT DOCUMENTS

| | | |
|---|---|---|
| 3,339,144 A | 8/1967 | Squires |
| 3,345,572 A | 10/1967 | Kaplan, I |
| 4,222,394 A | 9/1980 | Nagashima |
| 4,331,837 A | 5/1982 | Soumagne |
| 4,506,379 A | 3/1985 | Komatsu |
| 5,787,187 A | 7/1998 | Bouchard |
| 2003/0147538 A1* | 8/2003 | Elko ...................... H04R 3/005 381/91 |
| 2005/0114128 A1* | 5/2005 | Hetherington ...... G10L 21/0208 704/233 |
| 2015/0359468 A1* | 12/2015 | Bochner ................ A61B 5/123 600/559 |
| 2017/0318400 A1* | 11/2017 | Westermann .......... H04R 25/70 |

(Continued)

*Primary Examiner* — Lun-See Lao
(74) *Attorney, Agent, or Firm* — Daniel Anderson

(57) ABSTRACT

In one embodiment, an audio system can generate parametrically formulated noise signals. According to an embodiment, an audio system can both determine the hearing ability of an individual and increase the hearing ability of the individual by using parametrically formulated noise. According to an embodiment, an audio system can generate parametrically formulated noise having a power spectrum amplitude that is a function of an individual's hearing threshold across a range of frequencies as measured using parametrically formulated noise test signals.

3 Claims, 14 Drawing Sheets

(56) References Cited

U.S. PATENT DOCUMENTS

2019/0159702 A1\* 5/2019 Charaziak ............ A61B 5/6817
2020/0129094 A1\* 4/2020 Levine ............... A61B 1/00011

\* cited by examiner

SYSTEMS, DEVICES, AND METHODS FOR DETERMINING HEARING ABILITY AND TREATING HEARING LOSS

CROSS-REFERENCE TO RELATED APPLICATIONS

The present application is a divisional application of co-pending U.S. patent application Ser. No. 15/947,759 filed on Apr. 6, 2018, which claims the benefit of priority from: U.S. Provisional Application No. 62/482,645 filed on Apr. 6, 2017, all of which are hereby fully incorporated by reference.

BACKGROUND

The present invention relates, in general, to electronics and, more particularly, to audio systems, devices, and methods.

There are two main types of hearing loss: conductive hearing loss and sensorineural hearing loss. Conductive hearing loss can occur when sound is not conducted efficiently through the outer ear canal to the eardrum and the tiny bones (ossicles) of the middle ear. Sensorineural hearing loss can occur when there is damage to the inner ear, cochlea, or hearing nerve. Conventional hearing aids have employed sound amplification to mitigate the effects for both types of hearing loss. In fact, United States regulations define a hearing aid as a "wearable sound-amplifying device that is intended to compensate for impaired hearing" (21 CFR 874.3300(a)).

Sound processing in conventional hearing aids typically involves the amplification and compression of a sound signal. Generally, the sound signal is received through a microphone that forms part of the hearing aid or hearing aid system. The amplified and compressed sound signal which is produced by a hearing aid can be thought of as a "treatment signal" which is used to compensate for the hearing loss of the hearing aid user. The amount of amplification and compression which the hearing aid applies to the sound signal is typically determined by an audiologist who measures the hearing ability of an individual. Audiologists use pure tone "test signals" generated by an audiometer to determine the hearing ability of the individual. The pure tone test signals typically comprise pure tone signals at each of the following frequencies: 250 Hz, 500 Hz, 1000 Hz, 2000 Hz, 3000 Hz, and 4000 Hz. The pure tone signals are presented to an individual at varying sound levels in order to measure the individual's threshold of hearing at each of the above mentioned frequencies. These measured values are used to program the amplification and compression characteristics of the hearing aid.

Multiple errors and problems are created by the above described techniques, systems and processes. First, because the audiometer and the hearing aid are physically different acoustical sound systems, the measured values obtained by the audiometer do not necessarily translate faithfully into the operating environment of the hearing aid. Differences in calibration and resolution between the audiometer and the hearing aid, and even differences in microphone and speaker sensitivities from one hearing aid to the next, make it difficult to translate values from one acoustical system to another without introducing unknown amounts of error.

Second, the test signals of the audiometer and the treatment signals produced by the hearing aid are vastly different signals. Audiometric test signals are pure tone signals having a single frequency. These test signals are poor representations of the complex speech signals which are processed and produced by the hearing aid as treatment signals. Given this disparity, an individual's response to a pure tone test signal during an audiometric evaluation may be quite different from the individual's response to complex transient speech signals such as the amplified and compressed treatment signals generated by a hearing aid. Thus, further error can be introduced because the test signal does not resemble the treatment signal.

Third, audiometric testing is performed using discrete, pure tone, single frequency test signals. As described above, an audiometric exam generally tests for an individual's threshold of hearing at the discrete frequencies of 250 Hz, 500 Hz, 1000 Hz, 2000 Hz, 3000 Hz, and 4000 Hz. Calculations, such as linear extrapolations, are made to determine the individual's threshold of hearing at frequencies between the tested frequencies. This method can introduce errors when the individual's threshold of hearing at frequencies between the tested frequencies does not follow the linear or calculated extrapolation. This method fails to detect deviations such as notches in an individual's hearing.

Accordingly, it is desirable to have an audio system, device, and method for solving at least the above mentioned problems. It is desirable to have a single system or device capable of producing both the test and treatment signals. Furthermore, it is desirable to have test signal which corresponds to the treatment signal. Additionally, it is desirable to have a hearing test which can test a band of frequencies instead of discrete frequencies.

Figure 1:
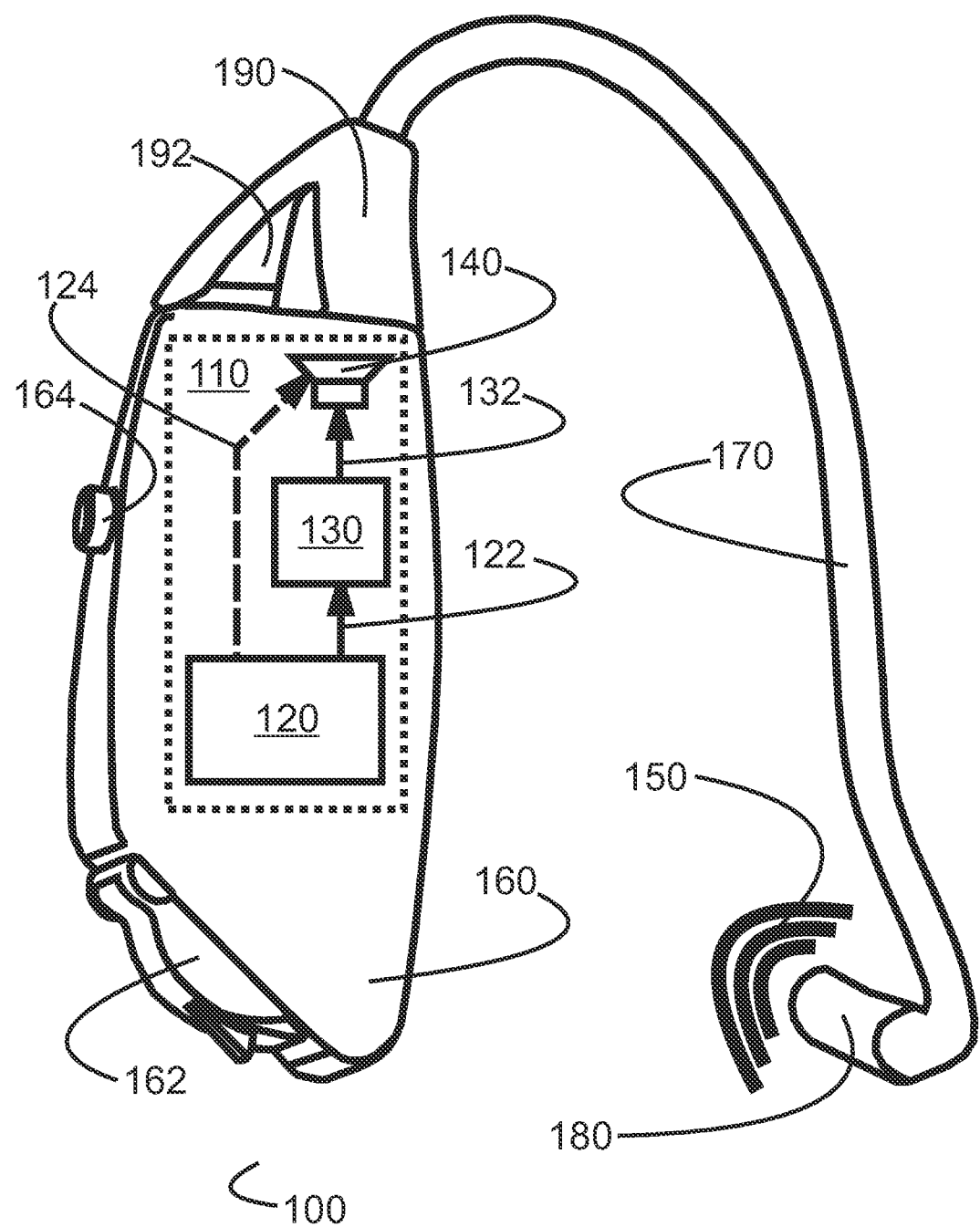
FIG. 1 illustrates a schematic diagram of an audio system.

The drawings and detailed description are provided in order to enable a person skilled in the applicable arts to make and use the invention. The systems, structures, circuits, devices, elements, schematics, signals, signal processing schemes, flow charts, diagrams, algorithms, frequency values and ranges, amplitude values and ranges, methods, source code, examples, etc., and the written descriptions are illustrative and not intended to be limiting of the disclosure. Descriptions and details of well-known steps and elements are omitted for simplicity of the description.

For simplicity and clarity of the illustration, elements in the figures are not necessarily drawn to scale, and the same reference numbers in different figures denote the same elements.

As used herein, the term and/or includes any and all combinations of one or more of the associated listed items. In addition, the terminology used herein is for the purpose of describing particular embodiments only and is not intended to be limiting of the disclosure. As used herein, the singular forms are intended to include the plural forms as well, unless the context clearly indicates otherwise. It will be further understood that the terms comprise, comprises, comprising, include, includes, and/or including, when used in this specification and claims, are intended to specify a non-exclusive inclusion of stated features, numbers, steps, acts, operations, values, elements, and/or components, but do not preclude the presence or addition of one or more other features, numbers, steps, acts, operations, values, elements, components, and/or groups thereof. It will be understood that, although the terms first, second, etc. may be used herein to describe various signals, portions of signals, ranges, members, and/or elements, these signals, portions of signals, ranges, members, and/or elements should not be limited by these terms. These terms are only used to distinguish one signal, portion of a signal, range, member, and/or element from another. Thus, for example, a first signal, a first portion of a signal, a first range, a first member, and/or a first element discussed below could be termed a second signal, a second portion of a signal, a second range, a second member, and/or a second element without departing from the teachings of the present disclosure. It will be appreciated by those skilled in the art that words, during, while, concurrently, and when as used herein related to audio systems, devices, methods, signal processing and so forth, are not limited to a meaning that an action, step, function, or process must take place instantly upon an initiating action, step, process, or function, but can be understood to include some small but reasonable delay, such as propagation delay, between the reaction that is initiated by the initial action, step, process, or function. Additionally, the terms during, while, concurrently, and when are not limited to a meaning that an action, step, function, or process only occur during the duration of another action, step, function, or process, but can be understood to mean a certain action, step, function, or process occurs at least within some portion of a duration of another action, step, function, or process or at least within some portion of a duration of an initiating action, step, function, or process or within a small but reasonable delay after an initiating action, step, function, or process. Furthermore, as used herein, the term range, may be used to describe a set of frequencies having an approximate upper and approximate lower bound, however, the term range may also indicate a set of frequencies having an approximate lower bound and no defined upper bound, or an upper bound which is defined by some other characteristic of the system. The term range may also indicate a set of frequencies having an approximate upper bound and no defined lower bound, or a lower bound which is defined by some other characteristic of the system. Reference to "one embodiment" or "an embodiment" means that a particular feature, structure, or characteristic described in connection with the embodiment is included in at least one embodiment of the present disclosure. Thus, appearances of the phrases "in one embodiment" or "in an embodiment" in various places throughout this specification are not necessarily all referring to the same embodiment, but in some cases it may. The use of words about, approximately or substantially means a value of an element is expected to be close to a stated value or position. However, as is well known in the art there are always minor variances preventing values or positions from being exactly stated. It is further understood that the embodiments illustrated and described hereinafter suitably may have embodiments and/or may be practiced in the absence of any element that is not specifically disclosed herein. Furthermore, it is understood that in some cases the embodiments illustrated and described hereinafter suitably may have embodiments and/or may be practiced with one or more of the illustrated or described elements, blocks, or signal processing steps omitted.

It is noted that while the invention described herein is described in context of audio systems, devices, and methods, the invention will also find application in many mechanical, electrical, power, and communications systems, devices, and methods.

Those skilled in the art will understand that as used herein, the terms add, added, adding, mix, mixed, or mixing may refer to any type of combination or summation of elements, signals, portions of signals, amplitudes, numbers, values, variables, sets, arrays, or objects. For example, the use of the terms add, added, adding, mix, mixed, or mixing may indicate electronic addition or mixing, numerical addition or mixing, digital addition or mixing, analog addition or mixing, or mechanical addition or mixing, such as air conduction mixing of acoustic signals.

Those skilled in the art will understand that as used herein, the terms audio device or audio system can refer to a stand-alone system or a subsystem of a larger system. A non-limiting list of example audio systems can include: hearing aids, personal sound amplification products, televisions, radios, cell phones, telephones, computers, laptops, tablets, vehicle infotainment systems, audio processing equipment and devices, personal media players, portable media players, audio transmission systems, transmitters, receivers, public address systems, media delivery systems, internet media players, smart devices, hearables, recording devices, subsystems within any of the above devices or systems, or any other device or system which processes audio signals.

As herein described or illustrated, components, elements, or blocks that are connected, coupled, or in communication may be electronically coupled so as to be capable of sending and/or receiving electronic signals between electronically coupled components, elements, or blocks, or linked so as to be capable of sending and/or receiving digital or analog signals, or information, between linked components, elements, or blocks. Coupling or connecting components, elements, or blocks as described or illustrated herein does not foreclose the possibility of including other intervening components, elements or blocks between the coupled or connected components, elements, or blocks. Coupling or connecting may be accomplished by hard wiring components elements or blocks, wireless communication between components, elements, or blocks, on-chip or on-board communications and the like.

Many electronic and mechanical alternatives are also possible to implement individual objectives of various components, elements, or blocks described or illustrated herein. For example, software or firmware operating on a digital device may be used to implement individual objectives of various components, elements, or blocks described or illustrated herein.

Multiple instances of embodiments described or illustrated herein may be used within a single audio device or system. As an example, multiple instances of embodiments described or illustrated herein may enable the processing of subdivisions of the various ranges of frequencies described herein. As another example, multiple instances of embodiments described or illustrated herein may enable a stereo audio device comprising a first instance of an embodiment for a right band and a second instance of an embodiment for a left band.

The inventor is fully informed of the standards and application of the special provisions of 35 U.S.C. §112(f). Thus, the use of the words "function," "means" or "step" in the Detailed Description of the Invention or claims is not intended to somehow indicate a desire to invoke the special provisions of 35 U.S.C. §112(f), to define the invention. To the contrary, if the provisions of 35 U.S.C. §112(f) are sought to be invoked to define the inventions, the claims will specifically and expressly state the exact phrases "means for" or "step for" and the specific function (e.g., "means for filtering"), without also reciting in such phrases any structure, material or act in support of the function. Thus, even when the claims recite a "means for . . . " or "step for . . . " if the claims also recite any structure, material, or acts in support of that means or step, or that perform the recited function, then it is the clear intention of the inventor not to invoke the provisions of 35 U.S.C. §112(f). Moreover, even if the provisions of 35 U.S.C. §112(f) are invoked to define the claimed inventions, it is intended that the inventions not be limited only to the specific structure, material or acts that are described in the illustrated embodiments, but in addition, include any and all structures, materials, or acts that perform the claimed function as described in alternative embodiments or forms of the invention, or that are well known present or later-developed, equivalent structures, material, or acts for performing the claimed function.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software, hardware or a combination of both. It should be noted that there are many different and alternative configurations, devices, and technologies to which the disclosed inventions may be applied. Thus, the full scope of the invention is not limited to the examples that are described below.

Various aspects of the present invention may be described in terms of functional block components and various signal processing steps. Such functional blocks may be realized by any number of hardware and/or software components configured to perform the specified functions and achieve the various results. In addition, various aspects of the present invention may be practiced in conjunction with any number of audio devices, and the systems and methods described are merely exemplary applications for the invention. Further, exemplary embodiments of the present invention may employ any number of conventional techniques for audio filtering, amplification, noise generation, modulation, summation, mixing, and the like.

It is noted that signal processing can be done in analog or digital form and various systems have a mixture of both analog and digital processes. The invention described herein can be implemented by analog or digital processes or a mixture of both analog and digital processes. Thus it is not a limitation of the invention that any particular process be implemented as either analog or digital. Those skilled in the art will readily see how to implement the invention using both analog and digital processes to achieve the results and benefits of the invention.

Various representative implementations of the present invention may be applied to any system for audio devices. For example, certain representative implementations may include: hearing aid devices and personal sound amplification products.

DETAILED DESCRIPTION OF THE DRAWINGS

FIG. 1 illustrates a schematic diagram of an audio system 100. According to various embodiments, audio system 100 can be configured to both determine the hearing ability of an individual and generate a treatment signal to assist or compensate the hearing loss of the individual based on the determined hearing ability of the individual.

According to an embodiment, audio system 100 can be configured to generate a pulsating noise sound 150 wherein pulsating noise sound 150 is perceived by an individual to pulsate with alternating periods of louder volume and diminished volume. According to an embodiment, audio system 100 can be configured to generate pulsating noise sound 150 using a pulsating parametrically formulated noise generator 110. According to an embodiment, pulsating parametrically formulated noise generator 110 can comprise a parametrically formulated noise generator 120, a pulsating modulator 130, and a receiver 140. Those skilled in the art will appreciate that there are many receiver 140 configurations including: balanced armature receivers, dynamic speakers, earphones, magnetic speakers, piezo speakers, electrostatic speakers, bone conduction speakers, electromechanical transducers, and the like. According to one embodiment, receiver 140 can be located within a housing 160. According to another embodiment, receiver 140 can be located external to housing 160.

According to an embodiment, parametrically formulated noise generator 120 can be configured to generate a first signal 122 comprising parametrically formulated noise substantially within a first range of frequencies. According to an embodiment, pulsating modulator 130 can be configured to receive from parametrically formulated noise generator 120 first signal 122. According to an embodiment, pulsating modulator 130 can be configured to generate a second signal 132 of pulsating parametrically formulated noise substantially within first range of frequencies. According to an embodiment, receiver 140 can be configured to receive from pulsating modulator 130 second signal 132 and generate pulsating noise sound 150. According to an embodiment, audio system 100 can be configured as a Behind-The-Ear (BTE) device consisting of a housing 160 for pulsating parametrically formulated generator 110 and tubing 170 to deliver pulsating noise sound 150 to an ear of an individual (not shown). Those skilled in the art will appreciate other configurations for audio system 100, comprising pulsating parametrically formulated noise generator 110, to deliver pulsating noise sound 150 to the ear including: a Hearing Aid (HA) configuration, an Invisible-In-Canal (IIC) configuration, a Completely-In-Canal (CIC) configuration, an In-The-Canal (ITC) configuration, an In-The-Ear (ITE) configuration, a Receiver-In-Canal (RIC) configuration, Behind-The-Ear (BTE) configuration, an On-The-Ear (OTE) configuration, a Body-Worn (BW) configuration, a wireless configuration, a headset configuration, an earphones configuration, a telephonics dynamics headphone (TDH) series audiometric earphones configuration, an insert earphone configuration, an audiometric insert earphone configuration, an earbud configuration, a speaker configuration, a Bone-Anchored (BA) configuration, a Bone-Conduction (BC) configuration, a Personal Sound Amplification Product (PSAP) configuration, an audiometer configuration, a telephone configuration, a cell phone configuration, a television configuration, a radio configuration, an audio system configuration, a media player configuration, a hearables configuration, a computer configuration, a laptop configuration, a tablet configuration, a smart device configuration, and the like.

According to an embodiment, housing 160 may include a battery 162. Those skilled in the art will appreciate that there are many battery 162 configurations including, for example, removable batteries and rechargeable batteries and may include a pivoting door for removing the batteries and external terminals for recharging the batteries and the like. According to an embodiment, housing 160 may include a first user interface 164. Those skilled in the art will appreciate that there are many first user interface 164 configurations including: push buttons, switches, rotary switches, rheostats, potentiometers, capacitive sense devices, touch devices, magnetic sense switches, proximity switches, reed switches, Hall effect sensors, phototransistors, photodiodes, optical sensors, infrared sensors, ultraviolet sensors, microphones, ultrasound devices, wireless devices, Bluetooth devices, motion sensing devices, accelerometers, Microelectromechanical Systems (MEMS) devices, and the like. According to an embodiment, user interfaces 164 such as wireless devices and Bluetooth devices may connect wirelessly to an external user interface, such as a cell phone, computer, keyboard, button, or the like. According to an embodiment, tubing 170 may be thin tubing having about a 0.8 mm inner diameter which when brought within an ear canal would be minimally occluding and maximize the natural amplification occurring with the pinna effect and ear canal resonance. According to an embodiment, tubing 170 may terminate with a tip 180. Those skilled in the art will appreciate that there are many tip 180 configurations including: wax guards, molds, domes, open domes, concha retainers, ear canal retainers, trumpets, Libby horns, preformed ends, directional ends, flexible tips, non-occluding molds, flanged tips, ridged tips, tapered tips, soft tips, and the like. According to an embodiment, tubing 170 may terminate at one end with an interface 190. Those skilled in the art will appreciate that there are many interface 190 configurations including: tubing fitting attachments, coupling attachments, tubing sockets, tubing couplers, molded sockets, removable interfaces, ear hooks, dampeners, stay-dry interfaces, built-in sound conduits 192 for microphones, and the like.

According to an embodiment, first user interface 164 can be configured to allow a user to identify the occurrence of a testing event or test event. According to various embodiments, a test event can include, for example, the user's perceived presence of pulsating noise sound, the user's perceived absence of a pulsating noise, or the user's perceived binaural balance or equal loudness of a pulsating noise sound in both ears. According to an embodiment, first user interface 164 can be configured to allow an individual to adjust the volume of pulsating noise sound in a first ear. According to an embodiment, first user interface 164 can be configured to allow an individual to adjust the volume of pulsating noise sound for a second ear. According to an embodiment, first user interface 164 can be configured to allow an individual to adjust the volume of pulsating noise sound for both a first and second ear. According to an embodiment, first user interface 164 can be configured to allow an individual to adjust the volume of pulsating noise sound for binaural balance between a first ear and a second ear. According to an embodiment, first user interface 164 can be configured to adapt the processing characteristics of a sound amplification device according to the hearing ability or hearing preferences determined for or by the individual. According to various embodiments, first user interface 164 can be configured to adjust characteristics of audio system 100, or to input information from a user of audio system 100.

According to various embodiments, audio system 100 can be configured to determine the hearing ability of an individual for a band of frequencies or for a plurality of bands of frequencies. According to an embodiment, audio system 100 can be configured to determine the hearing ability of each ear of an individual separately or both ears simultaneously. According to an embodiment, audio system 100 can comprise a one or more pulsating parametrically formulated noise generators such as pulsating parametrically formulated noise generator 110. According to an embodiment, pulsating parametrically formulated noise generator 110 can comprise one or more parametrically formulated noise generators 120. According to an embodiment, pulsating parametrically formulated noise generator 110 can comprise twelve parametrically formulated noise generators 120. According to an embodiment, each of the parametrically formulated noise generators can be configured to generate parametrically formulated noise within a selected range or band of frequencies in order to both determine the hearing ability of an individual and to generate a treatment signal.

According to an embodiment, parametrically formulated noise generators 120 can be configured to generate a plurality of parametrically formulated noise signals wherein each noise signal can comprise noise substantially within a particular frequency band. According to an embodiment, a plurality of parametrically formulated noise generators 120 can be configured to generate a plurality of parametrically formulated noise signals wherein each noise signal can comprise noise substantially within a particular frequency band. According to an embodiment, twelve parametrically formulated noise generators 120 can be configured to generate twelve parametrically formulated noise signals each corresponding to one of twelve frequency bands.

According to an embodiment, twelve frequency bands can be configured as follows:

Frequency Band 1: Random cycles of 400 Hz and 471 Hz
Frequency Band 2: Random cycles of 500 Hz and 604 Hz
Frequency Band 3: Random cycles of 627 Hz and 762 Hz
Frequency Band 4: Random cycles of 800 Hz and 942 Hz
Frequency Band 5: Random cycles of 1000 Hz and 1230 Hz
Frequency Band 6: Random cycles of 1280 Hz and 1524 Hz
Frequency Band 7: Random cycles of 1600 Hz and 1882 Hz
Frequency Band 8: Random cycles of 2000 Hz and 2370 Hz
Frequency Band 9: Random cycles of 2560 Hz and 2910 Hz
Frequency Band 10: Random cycles of 3200 Hz and 3764 Hz
Frequency Band 11: Random cycles of 4000 Hz and 4740 Hz
Frequency Band 12: Random cycles of 5120 Hz and 5818 Hz According to an embodiment, bands of frequencies can be chosen so that the power spectrums of individual frequency bands do not overlap sufficiently to create unwarranted power spectrum summation peaks or nulls between frequency bands. According to an embodiment, bands of frequencies can be chosen to have sufficient separation so that the power spectrum during the simultaneous operation of two or more parametrically formulated noise generators can be somewhat continuous across the composite power spectrum across two or more frequency bands. According to an embodiment, the hearing ability of an individual can be determined for all frequency bands for a first ear and/or for a second ear. According to an embodiment, the hearing ability of an individual can be determined for each frequency band one at a time. According to an embodiment, the hearing ability of an individual can be determined for each ear, one at a time, or both ears simultaneously.

According to various embodiments, audio system 100 can be configured to both determine the hearing ability of an individual and to generate a treatment 124 signal for the individual. According to various embodiments, audio system 100 can be configured so that the test signal or signals can correspond to the treatment signal or signals, for example, according to an embodiment, both the test signal and the treatment signal can comprise parametrically formulated noise. According to an embodiment, the volume of a pulsating noise sound 150 from pulsating parametrically formulated noise generator 110 for a band of frequencies can be tested and determined to be near, at, or just below the threshold of hearing for an individual; and a treatment signal 124 for the same or substantially the same band of frequencies, which may be for example a non pulsating noise sound, can be near, at, or substantially near the same volume. According to an embodiment, the treatment signal 124 can be generated from parametrically formulated noise generator 120. According to an embodiment, treatment signal 124 can be passed unaffected to receiver 140 through pulsating modulator 130 by nullifying pulsating modulator 130. According to another embodiment, treatment signal 124 can bypass pulsing modulator 130 as shown in FIG. 1. According to an embodiment, the treatment signal 124 may undergo additional processing before being presented to receiver 140. According to various embodiments, additional processing can comprise filtering, amplification, attenuation, summing or mixing with other signals or treatment signals, and/or conversion to digital or analog.

According to an embodiment, the simultaneous operation of a single parametrically formulated noise generator 120 or a plurality of parametrically formulated noise generators 120 can create a summation noise sound, treatment signal, or non-pulsating signal, which is also near, at, or just below the threshold of hearing for the individual for a plurality of frequency bands. According to an embodiment, the volume of each parametrically formulated noise generator 120 for each frequency band can be adjusted so as to correspond to the volume at which each pulsating noise sound 150 for each frequency band is tested and/or determined to be near, at, or below the threshold of hearing for the individual.

According to various embodiments, audio system 100 can be configured so that the treatment signal 124 is the signal or sound summation of one or more parametrically formulated noise generators 120 configured such that each treatment signal 124, or non pulsating noise sound from each of the parametrically formulated noise generators 120 is near, at, or just below the threshold of hearing for the plurality of frequency bands.

According to an embodiment, a treatment signal 124 from audio system 100 can be parametrically formulated noise contoured to an individual's specific frequency dependent thresholds of hearing.

According to an embodiment, audio system 100 can be configured to provide a treatment signal 124 comprising parametrically formulated noise contoured to an individual's specific frequency dependent thresholds of hearing where the power spectrum of the contoured parametrically formulated noise can be substantially or generally invariant during even short phoneme intervals. According to an embodiment, a treatment signal 124 can be combined with any additional energy from any speech phoneme, or other sound or signal, to "activate" and trigger a sensorineural hearing response. According to an embodiment, the parametrically formulated noise or treatment signal 124 can add to speech and the other signals received by the cochlea so that the cochlea can be activated by faint sound levels and respond faithfully to narrow frequency ranges.

According to an embodiment, audio system 100 can be configured to provide a treatment signal 124 comprising parametrically formulated noise contoured to an individual's specific frequency dependent thresholds to provide an effective treatment for sensorineural hearing loss and/or to provide a supplement or alternative to sound-amplification for the mitigation of sensorineural hearing loss or to reduce the use of sound-amplification to treat hearing loss.

According to an embodiment, a single audio system 100 can be configured to provide both a treatment signal 124 comprising parametrically formulated noise contoured to an individual's specific frequency dependent thresholds and a test signal 132 comprising parametrically formulated noise to determine the hearing ability of an individual so as to avoid changes in acoustic configuration which would require calibration and programming modifications.

According to an embodiment, audio system 100 can be configured to provide a treatment signal 124 comprising parametrically formulated noise contoured to an individual's specific frequency dependent thresholds delivered to the ear canal through a thin tube, for example, 0.8 mm inner diameter, from a Behind-The-Ear (BTE) device so as to minimally occlude the ear canal and maximize the natural amplification occurring with the pinna effect and ear canal resonance.

According to an embodiment, a length of a thin tube from a Behind-The-Ear (BTE) device can first be adjusted to the individual's ear geometry because the length of the thin tube can affects its acoustic impedance and the individual's hearing ability can be determined after the length of the thin tube has been adjusted.

According to an embodiment, an individual with hearing loss can self-test hearing ability using audio system 100 and related parameters and settings for audio system 100 can be set or programmed. According to an embodiment, an individual can also reset or reprogram audio system 100 to compensate for changing hearing loss, to compensate for changing receiver (speaker) sensitivity over time, to compensate for changing microphone (see, for example 930 in FIG. 9) sensitivity over time, or to compensate for the individual's own perception and response errors during testing.

According to various embodiments, audio system 100 can be configured to provide a treatment signal 124 comprising parametrically formulated noise contoured to an individual's specific frequency dependent thresholds and can also be configured to add sound amplification with a sound amplification device (see, for example 920 in FIG. 9) which can also eliminate the need for compression for higher frequency bands.

According to various embodiments, audio system 100 can be configured to provide a treatment signal 124 comprising parametrically formulated noise contoured to an individual's specific frequency dependent thresholds and can also be configured to add wireless sound amplification with a wireless sound amplification device (see, for example 1020 in FIG. 10) which can also eliminate the need for compression for higher frequency bands.

Figure 2:
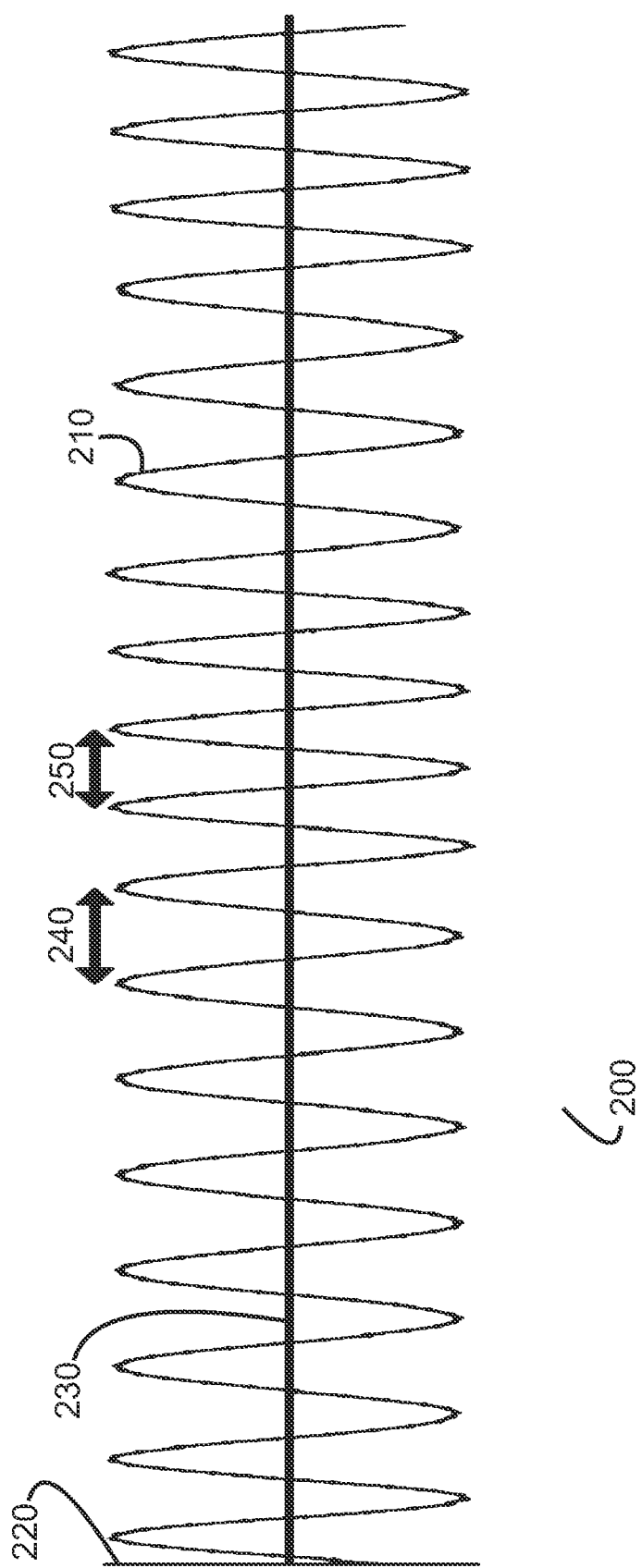
FIG. 2 illustrates a waveform graph of a parametrically formulated noise signal.

FIG. 2 illustrates a waveform graph 200 of a parametrically formulated noise signal 210. According to an embodiment, a parametrically formulated noise generator 120 (see FIG. 1) can be configured to generate a first signal 122 (see FIG. 1) of parametrically formulated noise 210. Parametrically formulated noise signal 210 is shown having an amplitude 220 plotted as a function of time 230. According to an embodiment, parametrically formulated noise signal 210 comprises a noise signal substantially within a first range of frequencies, generated by time ordering, in a random or pseudorandom order, a plurality of periodic waves having frequencies within a first range of frequencies. According to an embodiment, parameters representing a ratio of duration for each of the plurality of periodic waves can be selected in order to control the power spectrum amplitude of parametrically formulated noise signal 210 across a range of frequencies. According to an embodiment, parametrically formulated noise signal 210 can be a time ordered, random or pseudorandom, sequence of a first periodic wave having a first period or first frequency 240 and a second periodic wave having a second period or second frequency 250. According to another embodiment parametrically formulated noise signal 210 can comprise additional periodic waves having periods or frequencies within a range of frequencies.

According to an embodiment, parametrically formulated noise signal 210 can be generated utilizing a memory or storage device and a processor. The storage device can store, for example, a first series of values corresponding to the amplitude of a first periodic wave having a first frequency sampled according to a first sampling rate over a first period of time. Additionally, the storage device can store, for example, a second series of values corresponding to the amplitude of a second periodic wave having a second frequency sampled according to the first sampling rate over a second period of time. According to an embodiment, a storage device can store plurality of series of values corresponding to the amplitude of a plurality of periodic waves having a plurality of frequencies sampled according to various sampling rates over various periods of time. According to an embodiment, a processor can be coupled to the memory device and configured to recursively make a random selection between, for example, the first periodic wave and the second periodic wave and output a parametrically formulated noise signal, such as parametrically formulated noise signal 210, comprising the series of values corresponding to the randomly or pseudorandomly selected periodic signal. According to an embodiment, such a parametrically formulated noise signal can have a power spectrum that has a generally or substantially uniform amplitude between the first frequency and the second frequency. Furthermore, the processor can be configured to modify the amplitude of the parametrically formulated noise signal using a third series of values stored on the storage device which can correspond to levels for amplitude modification so as to modulate the parametrically formulated noise signal and create a pulsing amplitude with alternating periods of greater amplitude and diminished amplitude. The processor can then output such a pulsating parametrically formulated noise signal.

Figure 3:
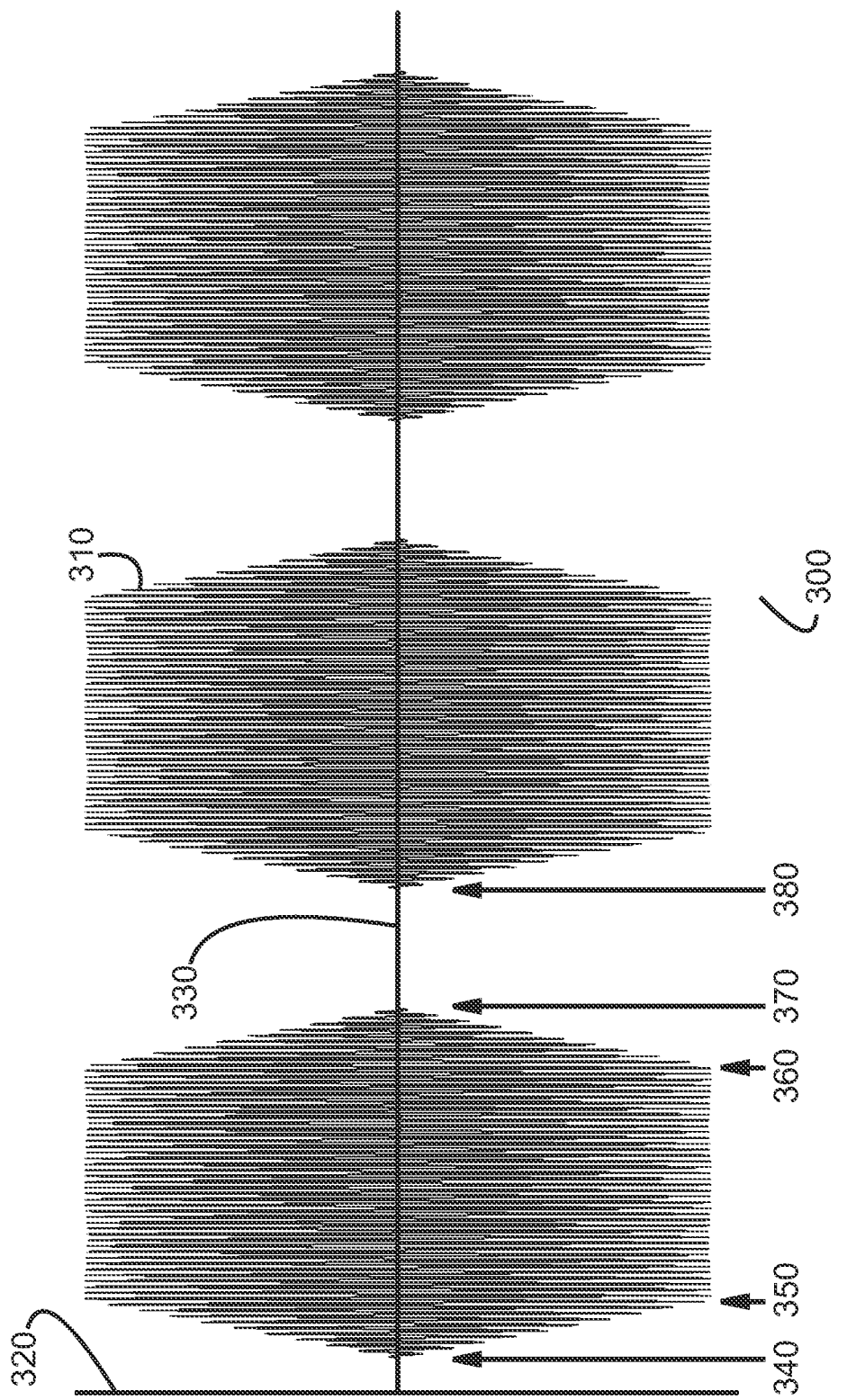
FIG. 3 illustrates an example waveform graph of a pulsating noise sound.

FIG. 3 illustrates a waveform graph 300 of pulsating noise sound 310. According to an embodiment, a pulsating modulator 130 (see FIG. 1) can be configured to generate second signal 132 (see FIG. 1) of pulsating parametrically formulated noise and receiver 140 (see FIG. 1) can be configured to receive from pulsating modulator 130 (see FIG. 1) second signal 132 (see FIG. 1) which, according to an embodiment, can be represented by pulsating noise sound 310. Pulsating noise sound 310 is shown having an amplitude 320 plotted as a function of time 330. Pulsating noise sound 310 is perceived by the individual to pulsate with alternating periods of louder volume and diminished volume. According to an embodiment, pulsating noise sound 310 has periods of diminished volume such as between a first time 340 and a second time 350; between a third time 360 and a fourth time 370; and, between fourth time 370 and a fifth time 380. According to an embodiment, pulsating noise sound 310 has periods of louder volume such as between second time 350 and third time 360. According to an embodiment, pulsating noise sound 310 between first time 340 and second time 350 can be between about 20 milliseconds and 50 milliseconds. According to an embodiment, pulsating noise sound 310 between first time 340 and second time 350 can be near instantaneous, zero, or near zero milliseconds. According to an embodiment, pulsating noise sound 310 between first time 340 and second time 350 can be about 40 milliseconds. According to an embodiment, pulsating noise sound 310 between first time 340 and a second time 350 may rise progressively without discontinuities. According to an embodiment, pulsating noise sound 310 between first time 340 and a second time 350 can rise in about ½ dB (decibel) steps about every ½ millisecond. According to an embodiment, pulsating noise sound 310 between third time 360 and fourth time 370 can be between about 20 milliseconds and 50 milliseconds. According to an embodiment, pulsating noise sound 310 between third time 360 and fourth time 370 can be near instantaneous, zero, or near zero milliseconds. According to an embodiment, pulsating noise sound 310 between third time 360 and fourth time 370 can be about 40 milliseconds. According to an embodiment, pulsating noise sound 310 between third time 360 and fourth time 370 may fall progressively without discontinuities. According to an embodiment, pulsating noise sound 310 between third time 360 and fourth time 370 can fall in about ½ dB steps about every ½ millisecond. According to an embodiment, pulsating noise sound 310 between second time 350 and third time 360 can be greater than about 100 milliseconds. According to an embodiment, pulsating noise sound 310 between second time 350 and third time 360 can be about 120 milliseconds. According to an embodiment, pulsating noise sound 310 between second time 350 and third time 360 can be about 170 milliseconds. According to an embodiment, pulsating noise sound 310 between fourth time 370 and fifth time 380 can be about 0 milliseconds or greater. According to an embodiment, pulsating noise sound 310 between fourth time 370 and fifth time 380 can be about 10 milliseconds. According to an embodiment, pulsating noise sound 310 between fourth time 370 and fifth time 380 can be about 0 milliseconds. According to an embodiment, pulsating noise sound 310 amplitude differences between first time 340 and second time 350 can be about 20 dB or greater. According to an embodiment, pulsating noise sound 310 amplitude differences between third time 360 and fourth time 370 can be about 20 dB or greater. According to an embodiment, pulsating noise sound 310 amplitude differences between first time 340 and second time 350 can be about 40 dB. According to an embodiment, pulsating noise sound 310 amplitude differences between third time 360 and fourth time 370 can be about 40 dB. According to an embodiment, the amplitude of pulsating noise sound 310 between fourth time 370 and fifth time 380 can be zero, near zero, or any amplitude greater than zero. Those skilled in the art will appreciate that many different techniques and designs can be used to create pulsating noise sound 310 including different modulation envelopes, timings, durations, and/or amplitude differences.

Figure 4:
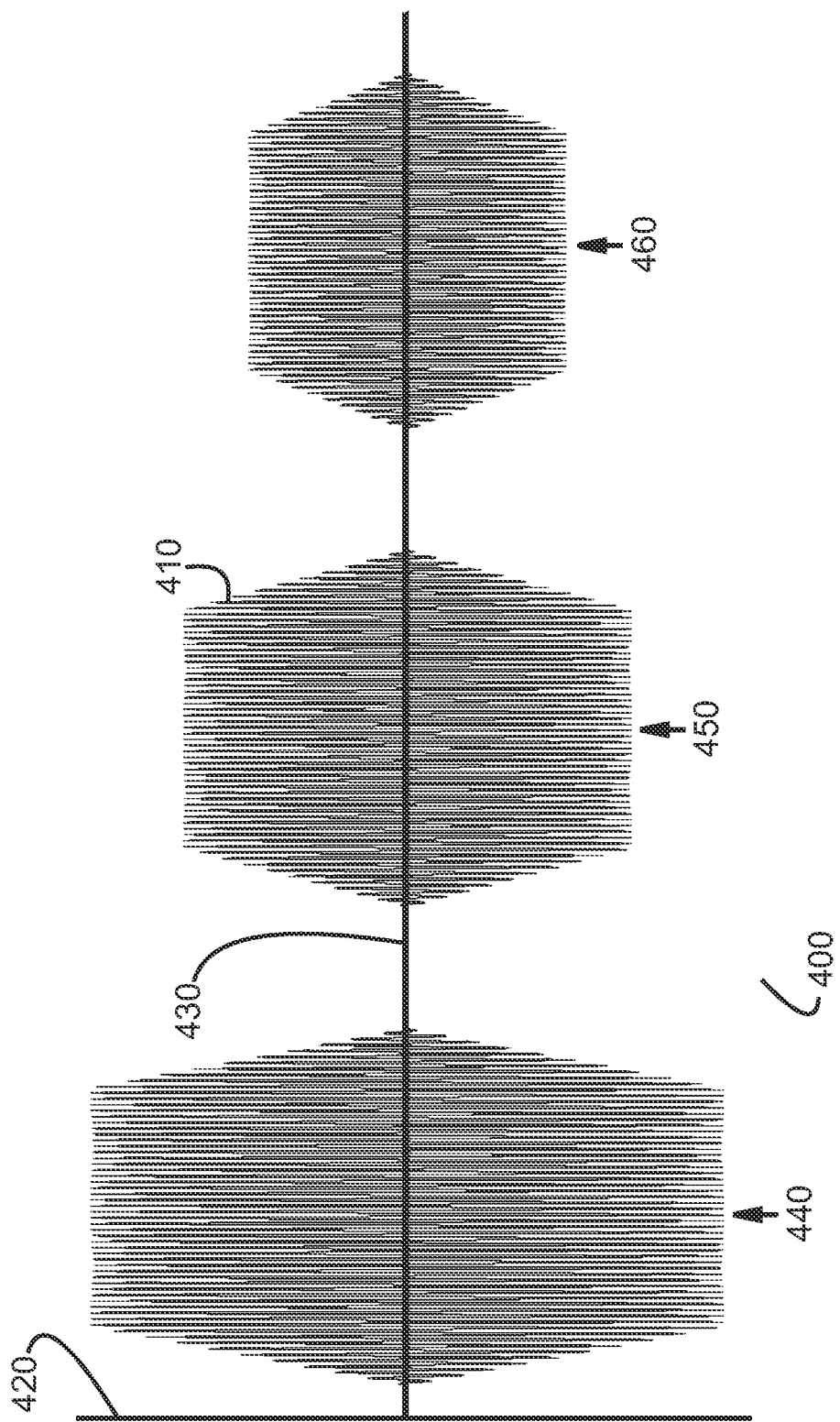
FIG. 4 illustrates an example waveform graph of a pulsating noise sound diminishing in volume over time.

FIG. 4 illustrates a waveform graph 400 of pulsating noise sound 410 wherein pulsating noise sound 410 diminishes in volume over time. According to an embodiment, a pulsating modulator 130 (see FIG. 1) can be configured to generate a second signal 132 (see FIG. 1) of pulsating parametrically formulated noise and receiver 140 (see FIG. 1) can be configured to receive from pulsating modulator 130 (see FIG. 1) second signal 132 (see FIG. 1) which, according to an embodiment, can be represented by pulsating noise sound 410 wherein pulsating noise sound 410 diminishes in volume over time. Pulsating noise sound 410 is shown having an amplitude 420 plotted as a function of time 430. According to an embodiment, pulsating noise sound 410 can be perceived by the individual to pulsate with alternating periods of louder volume and diminished volume. According to an embodiment, pulsating noise sound 410 can be perceived to diminish in volume over time. According to an embodiment, a first plurality of pulses (not shown) can have a first amplitude or first volume and can be followed by a second plurality of pulses (not shown) having a second amplitude or second volume which is less than the first amplitude or first volume. According to an embodiment, pulsating noise sound 410 can be configured to diminish in volume over time between a first pulse 440 and a second pulse 450 and between second pulse 450 and a third pulse 460. According to an embodiment, a first pulse 440 can have an average amplitude greater than a second pulse 450. According to an embodiment, pulsating noise sound 410 can be configured to diminish in volume over time. According to an embodiment, pulsating noise sound 410 can pulse at a rate of 4 pulses per second. According to an embodiment, the time between first pulse 440 and second pulse 450 can be about 250 milliseconds and the time between second pulse 450 and third pulse 460 can be about 250 milliseconds. According to an embodiment, pulsating noise sound 410 wherein pulsating noise sound 410 diminishes in volume over time, can be configured to diminish at a rate of 2 dB per second. According to an embodiment, the volume difference between first pulse 440 and second pulse 450 can be about ½ dB and the volume difference between second pulse 450 and third pulse 460 can be about ½ dB. Those skilled in the art will appreciate that many different techniques and designs can be used to create pulsating noise sound 410 which can be configured to diminish in volume over time including: diminishing continuously, diminishing with groups of pulses, and, diminishing with different timings, rates, amounts, durations, and/or amplitude differences.

Figure 5:
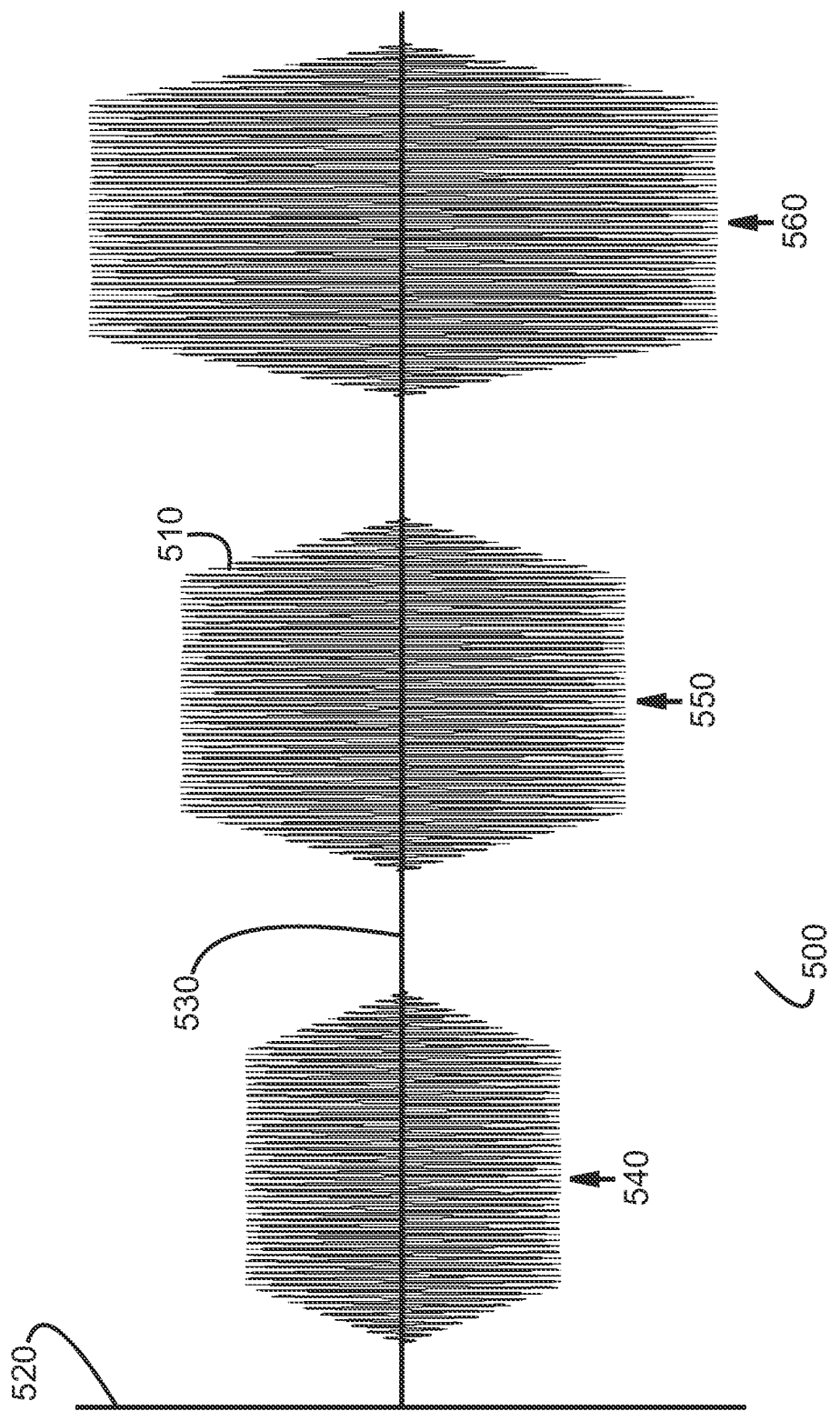
FIG. 5 illustrates an example waveform graph of a pulsating noise sound increasing in volume over time.

FIG. 5 illustrates a waveform graph 500 of pulsating noise sound 510 wherein the pulsating noise sound 510 increases in volume over time. According to an embodiment, pulsating modulator 130 (see FIG. 1) can be configured to generate second signal 132 (see FIG. 1) of pulsating parametrically formulated noise and receiver 140 (see FIG. 1) can be configured to receive from pulsating modulator 130 (see FIG. 1) second signal 132 (see FIG. 1) which, according to an embodiment, can be represented by pulsating noise sound 510 wherein the pulsating noise sound 510 increases in volume over time. Pulsating noise sound 510 is shown having an amplitude 520 plotted as a function of time 530. According to an embodiment, pulsating noise sound 510 can be perceived by the individual to pulsate with alternating periods of louder volume and diminished volume. Pulsating noise sound 510 can be perceived to increase in volume over time. According to an embodiment, a first plurality of pulses (not shown) can have a first amplitude or first volume and can be followed by a second plurality of pulses (not shown) having a second amplitude or second volume which is greater than the first amplitude or first volume. According to an embodiment, pulsating noise sound 510 can be configured to increase in volume over time between a first pulse 540 and a second pulse 550 and between second pulse 550 and a third pulse 560. According to an embodiment, pulsating noise sound 510 wherein the pulsating noise sound 510 increases in volume over time can be configured to pulse at a rate of about 5 pulses per second. According to an embodiment, the time between first pulse 540 and second pulse 550 can be about 200 milliseconds and the time between second pulse 550 and third pulse 560 can be about 200 milliseconds. According to an embodiment, pulsating noise sound 510 wherein the pulsating noise sound 510 increases in volume over time can be configured to increase at a rate of about 10 dB per second. According to an embodiment, the volume difference between first pulse 540 and second pulse 550 can be about 2 dB and the volume difference between second pulse 550 and third pulse 560 can be about 2 dB. Those skilled in the art will appreciate that many different techniques and designs can be used to create pulsating noise sound 510 which can increase in volume over time including: increasing continuously, increasing with groups of pulses, and increasing with different timings, rates, amounts, durations, and/or amplitude differences.

Figure 6:
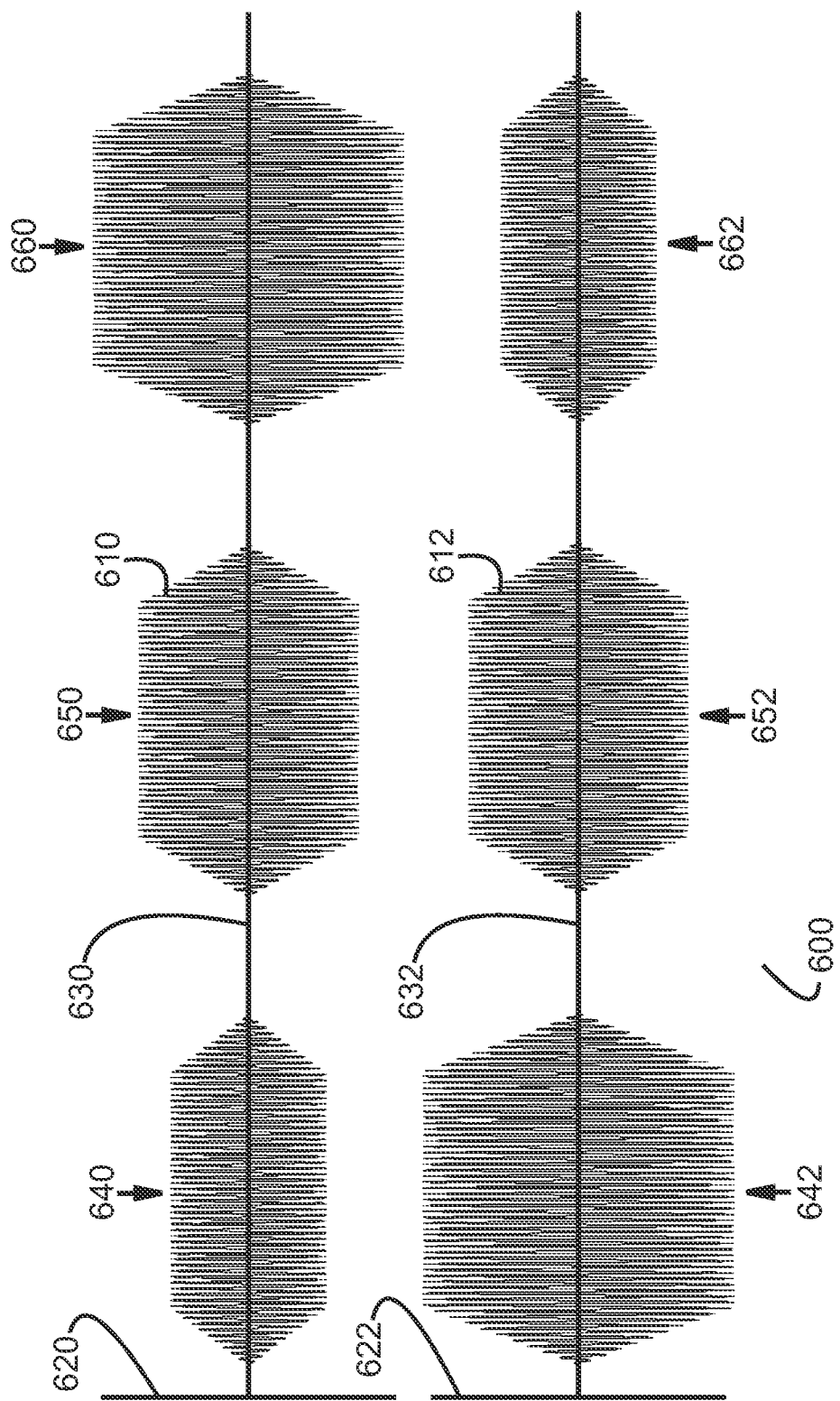
FIG. 6 illustrates example waveform graphs of pulsating noise sounds.

FIG. 6 illustrates a waveform graph 600 of pulsating noise sounds 610 and 612 wherein pulsating noise sound 610 increases in volume over time in a first ear of an individual and wherein pulsating noise sound 612 decreases in volume over time in a second ear of an individual. Pulsating noise sound 610 is shown having an amplitude 620 plotted as a function of time 630. Pulsating noise sound 612 is shown having an amplitude 622 plotted as a function of time 632. According to an embodiment, time 630 and time 632 can be simultaneous. According to an embodiment, pulsating noise sound 610 can be perceived by the individual to pulsate in first ear with alternating periods of louder volume and diminished volume. According to an embodiment, pulsating noise sound 612 can be perceived by the individual to pulsate in second ear with alternating periods of louder volume and diminished volume. According to an embodiment, pulsating noise sound 610 can be perceived by the individual to increase in volume over time relative to the volume of the pulsing noise sound 612. According to an embodiment, pulsating noise sound 612 may be perceived to decrease in volume over time relative to the volume of the pulsing noise sound 610. According to an embodiment, pulsating noise sound 610 can be presented to a first ear and pulsating noise sound 612 can be presented to a second ear wherein the pulsating noise sound 610 increases in volume over time for a first pulse 640, a second pulse 650, and a third pulse 660 and wherein the pulsating noise sound 612 decreases in volume over the same time for a fourth pulse 642, a fifth pulse 652, and a sixth pulse 662. According to an embodiment, an audio system can be configured to allow a user to control, via a user interface, the increasing of volume of a first pulsating noise sound while simultaneously decreasing or maintaining the volume of a second pulsating noise sound until the user perceives the relative volumes of the first and second pulsating noise sounds to be equal or balanced. Those skilled in the art will appreciate that many different techniques and designs can be used to create pulsating noise sound 610 in first ear which increases in volume over time relative to pulsating noise sound 612 in second ear including: increasing continuously, increasing with groups of pulses, and increasing with different timings, rates, amounts, durations, and/or amplitude differences.

Figure 7:
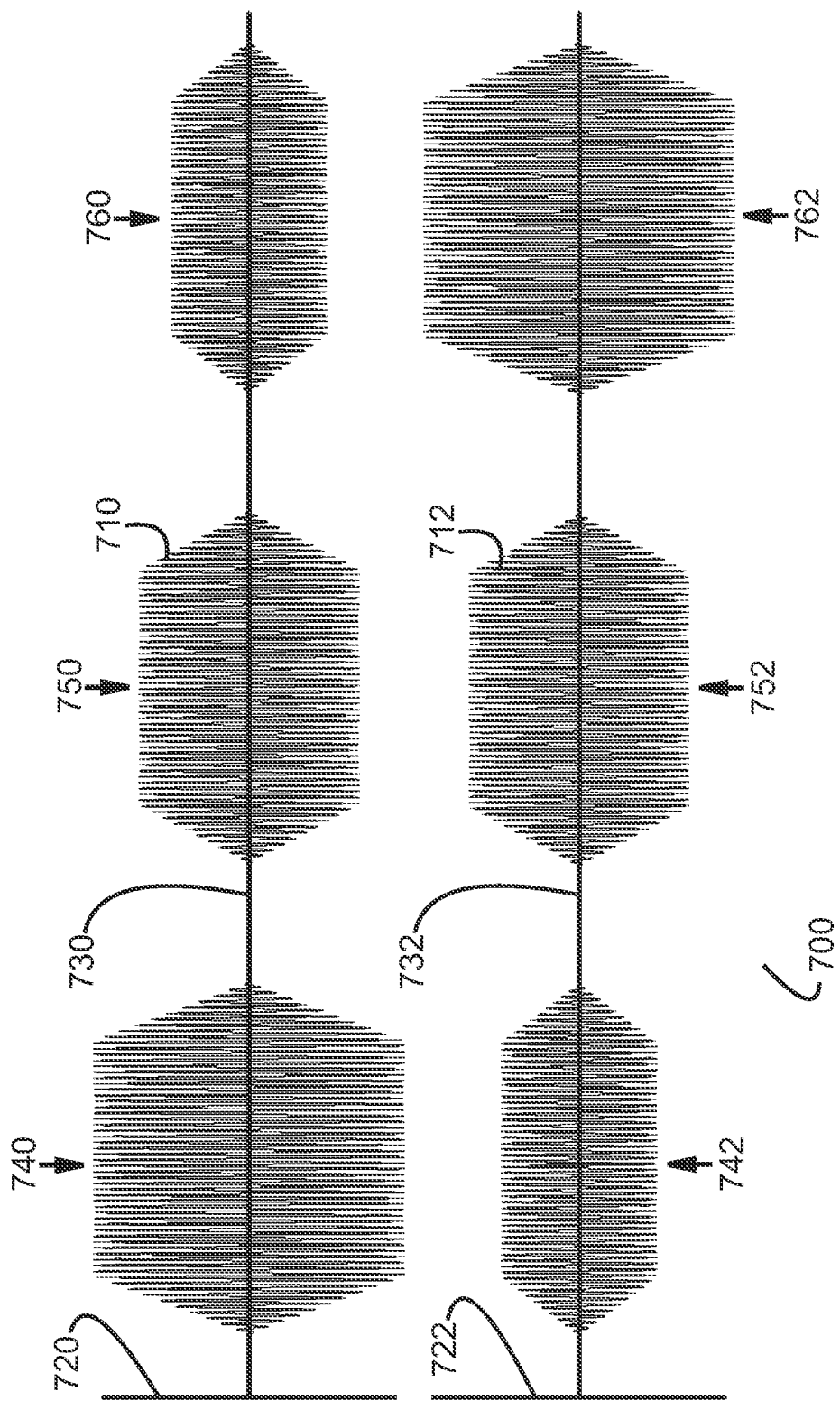
FIG. 7 illustrates example waveform graphs of pulsating noise sounds.

FIG. 7 illustrates a waveform graph 700 of pulsating noise sounds 710 and 712 wherein pulsating noise sound 710 decreases in volume over time in a first ear of an individual and wherein pulsating noise sound 712 increases in volume over time in a second ear of an individual. Pulsating noise sound 710 is shown having an amplitude 720 plotted as a function of time 730. Pulsating noise sound 712 is shown having an amplitude 722 plotted as a function of time 732. According to an embodiment, time 730 and time 732 can be simultaneous. According to an embodiment, pulsating noise sound 710 can be perceived by the individual to pulsate in first ear with alternating periods of louder volume and diminished volume. According to an embodiment, pulsating noise sound 712 can be perceived by the individual to pulsate in second ear with alternating periods of louder volume and diminished volume. According to an embodiment, pulsating noise sound 710 can be perceived by the individual to decrease in volume over time relative to the volume of the pulsing noise sound 712. According to an embodiment, pulsating noise sound 712 may be perceived to increase in volume over time relative to the volume of the pulsing noise sound 710. According to an embodiment, pulsating noise sound 710 can be presented to a first ear and pulsating noise sound 712 can be presented to a second ear wherein the pulsating noise sound 710 decreases in volume over time for a first pulse 740, a second pulse 750, and a third pulse 760 and wherein the pulsating noise sound 712 increases in volume over the same time for a fourth pulse 742, a fifth pulse 752, and a sixth pulse 762. According to an embodiment, an audio system can be configured to allow a user to control, via a user interface, the increasing of volume of a first pulsating noise sound while simultaneously decreasing or maintaining the volume of a second pulsating noise sound until the user perceives the relative volumes of the first and second pulsating noise sounds to be equal or balanced. Those skilled in the art will appreciate that many different techniques and designs can be used to create pulsating noise sound 710 in first ear which decreases in volume over time relative to pulsating noise sound 712 in second ear including: increasing continuously, increasing with groups of pulses, and increasing with different timings, rates, amounts, durations, and/or amplitude differences.

Figure 8:
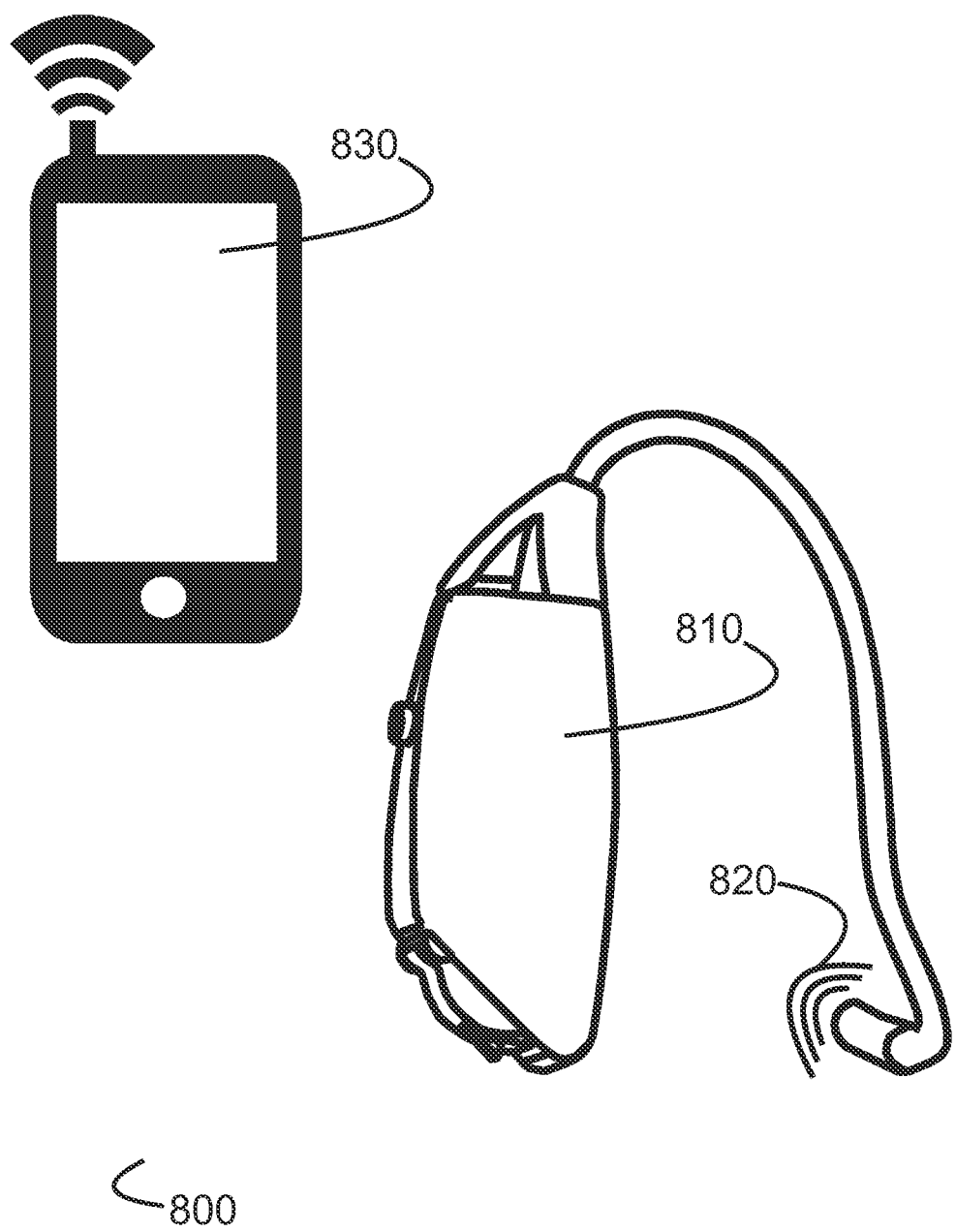
FIG. 8 illustrates a schematic diagram of an audio system.

FIG. 8 illustrates a schematic diagram 800 of an audio system 810. According to an embodiment, audio system 810 can produce a sound 820 and can be connected to, wired or wirelessly, a user input device or user interface 830. According to an embodiment, user interface 830 can be used in connection with audio system 810 to determine of hearing ability of an individual. According to various embodiments, user interface 830 can be a smart phone, a laptop computer, a computer, a tablet, a light device, an infrared device, an ultra-violet device, a sound device, a clicker device, a button, an individual making sound, a microphone, a camera, a motion tracker, a motion sensor, and/or a remote control or any other user input device known to those of ordinary skill in the art. According to an embodiment, user interface 830 can communicate with audio system 810 via wireless or wired communication. According to an embodiment, user interface 830 can be configured to enable a user to identify a perceived presence of pulsating noise sound. According to an embodiment, user interface 830 can be configured to enable a user to identify a perceived absence of pulsating noise sound. According to an embodiment, user interface 830 can be configured to enable a user to identify when pulsating noise sound is perceived to be equally loud in both ears. According to an embodiment, user interface 830 can be configured to enable a user to control or adjust the volume of pulsating noise sound for a first ear. According to an embodiment, user interface 830 can be configured to enable a user to adjust the volume of pulsating noise sound for a second ear. According to an embodiment, user interface 830 can be configured to enable a user to control or adjust the volume of a first pulsating noise sound for a first ear while simultaneously adjusting or maintaining the volume of a second pulsating noise in a second ear such that a user can adjust the relative volume between the pulsating noise sounds until they are perceived as equal in volume or binaurally balanced between the user's first ear and second ear. According to an embodiment, user interface 830 can be configured to enable a user to change or adapt the processing characteristics of a sound amplification device according to the hearing ability determined for the individual.

Figure 9:
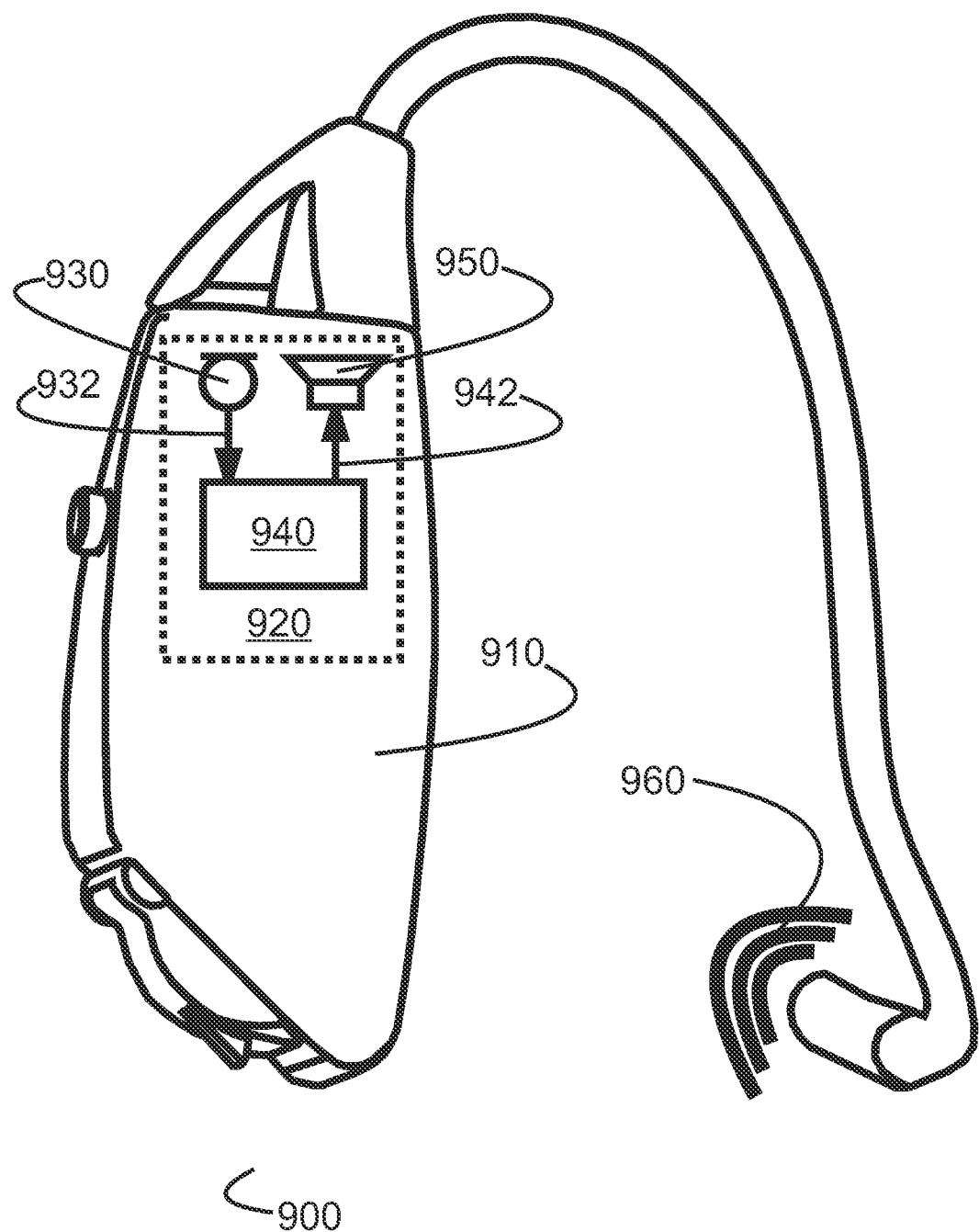
FIG. 9 illustrates a schematic diagram of an audio system.

FIG. 9 illustrates a schematic diagram 900 of an audio system 910. According to an embodiment, audio system 910 can be configured to test or determine the hearing ability of a user using parametrically formulated noise. According to an embodiment, audio system 910 can be configured to test or determine the hearing ability of a user using pulsating parametrically formulated noise. According to an embodiment, audio system 910 can be configured to administer a hearing test to a user by providing the user with a series of test signals comprising parametrically formulated noise and receiving input from the user in response to the test signals. For example, audio system 910 can be configured to provide to a user a pulsating noise sound within a first band of frequencies which is decreasing in volume over time. A user can then provide input to audio system 910 via a user interface at a moment in time when the user detects that he or she can no longer perceive or hear the pulsating noise sound. Audio system 910 can be configured to receive a user's response to the test signal and can store data representing or corresponding to the user's response to the test signal. Audio system 910 can receive and store additional data by providing the user with additional tests and then receiving and storing the user's response to the additional test signals. According to an embodiment, data representing the user's responses to tests signals can be stored on a memory device or storage device. According to an embodiment, a storage device can form a part of audio system 910 or can be located external to audio system 910. According to an embodiment, audio system 910 can use the data representing the user's hearing ability to generate a parametrically formulated noise signal contoured to the user's specific frequency dependent thresholds of hearing. Such parametrically formulated noise signal can be used as a treatment signal to increase the user's hearing ability. According to an embodiment, audio system 910 can also comprise a sound amplification device 920. Sound amplification device 920 can comprise a microphone 930 configured to receive air-conduction sound and generate a first signal 932. Sound amplification device 920 can comprise a processor 940 configured to receive first signal 932, process the signal, and generate a second signal 942. According to an embodiment, processor 940 can be a digital signal processor or an analog signal processor. In the case of a digital signal processor, an analog-to-digital converter can be used to convert first signal 932 to a digital signal. Furthermore, in the case of a digital signal processor, a digital-to-analog converter can be used to convert a second signal 942 to an analog signal. Sound amplification device 920 can also comprise a receiver 950. Receiver 950 can be configured to receive second signal 942 and generate a sound 960. According to an embodiment, audio system 910 can be configured as a Behind-The-Ear (BTE) device. According to various embodiment, audio system 910 may also comprise a Hearing Aid (HA), an Invisible-In-Canal (IIC) device, a Completely-In-Canal (CIC) device, an In-The-Canal (ITC) device, an In-The-Ear (ITE) device, a Receiver-In-Canal (RIC) device, Behind-The-Ear (BTE) device, an On-The-Ear (OTE) device, a Body-Worn (BW) device, a wireless device; a headset, earphones, a TDH series audiometric earphones device, an insert earphone device, an audiometric insert earphone device, an earbud, a speaker, a Bone-Anchored (BA) device, a Bone-Conduction (BC) device, a Personal Sound Amplification Product (PSAP) device, an audiometer, a telephone, a cell phone, a television, a radio, an audio system, a media player, a hearables device, a wearable audio device, a computer, a tablet, a laptop, a smart device and/or any other audio device and the like.

Figure 10:
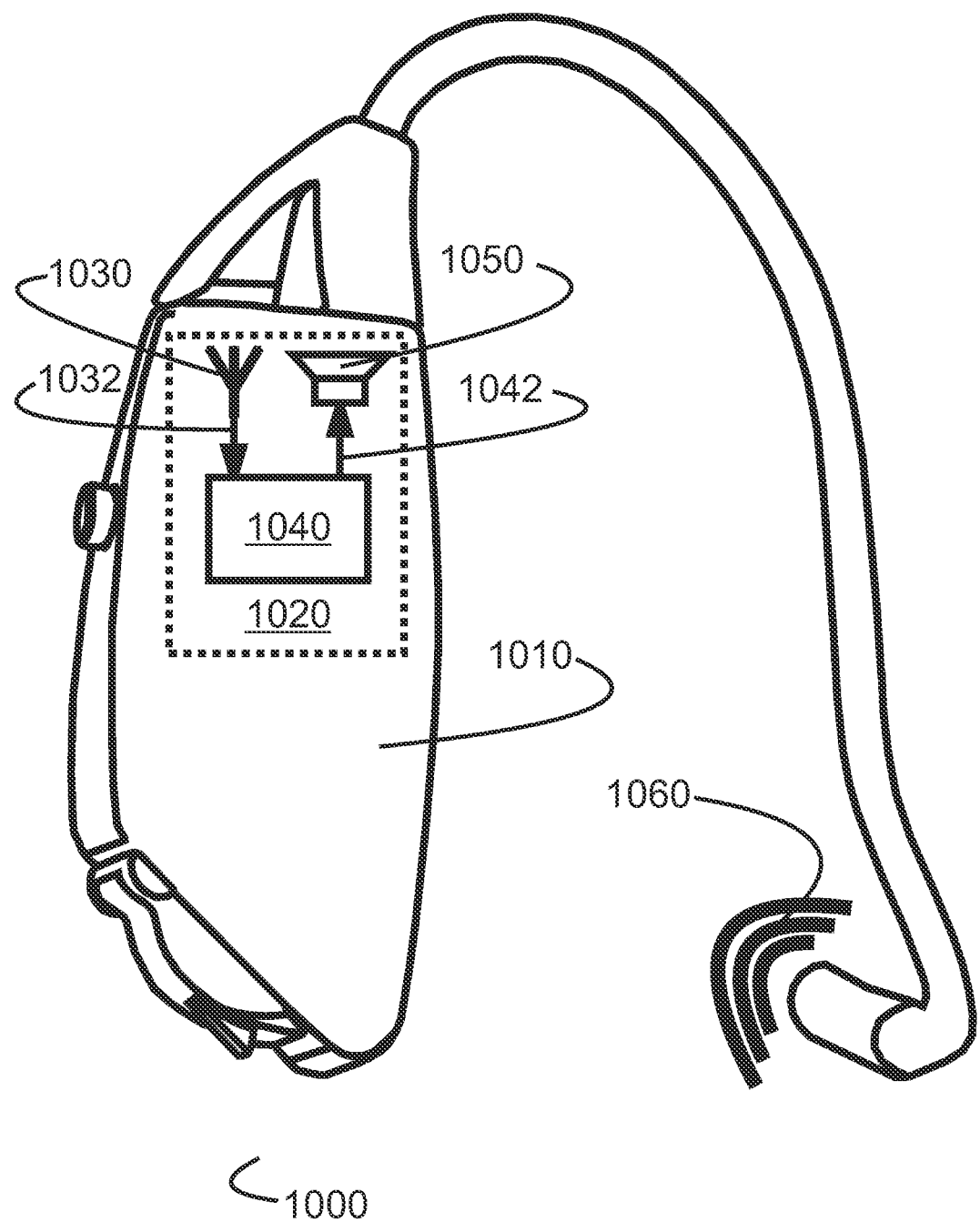
FIG. 10 illustrates a schematic diagram of an audio system.

FIG. 10 illustrates a schematic diagram 1000 of an audio system 1010. According to an embodiment, audio system 1010 can be configured to test or determine the hearing ability of a user using parametrically formulated noise. According to an embodiment, audio system 1010 can be configured to test or determine the hearing ability of a user using pulsating parametrically formulated noise. According to an embodiment, audio system 1010 can be configured to administer a hearing test to a user by providing the user with a series of test signals comprising parametrically formulated noise and receiving input from the user in response to the test signals. For example, audio system 1010 can be configured to provide to a user a pulsating noise sound within a first band of frequencies which is decreasing in volume over time. A user can then provide input to audio system 1010 via a user interface at a moment in time when the user detects that he or she can no longer perceive or hear the pulsating noise sound. Audio system 1010 can be configured to receive a user's response to the test signal and can store data representing or corresponding to the user's response to the test signal. Audio system 1010 can receive and store additional data by providing the user with additional tests and then receiving and storing the user's response to the additional test signals. According to an embodiment, data representing the user's responses to tests signals can be stored on a memory device or storage device. According to an embodiment, a storage device can form a part of audio system 1010 or can be located external to audio system 1010. According to an embodiment, audio system 1010 can use the data representing the user's hearing ability to generate a parametrically formulated noise signal contoured to the user's specific frequency dependent thresholds of hearing. Such parametrically formulated noise signal can be used as a treatment signal to increase the user's hearing ability. According to an embodiment, audio system 1010 can also comprise a sound amplification device 1020. Sound amplification device 1020 can comprise a wireless receiver, wireless sensor, or antenna 1030 configured to pick up or receive a wireless signal and provide the received signal as first signal 1032 to a processor 1040. Audio system 1010 can be configured to receive many different types of wireless signals, for example, radio signals, Bluetooth signals, microwave signals, optical signals, infrared signals, telecoil signals, induction loop signals, and the like. Processor 1040 can be configured to receive the first signal 1032, process the signal, and generate a second signal 1042. According to an embodiment, processor 1040 can be a digital signal processor or an analog signal processor. In the case of a digital signal processor, an analog-to-digital converter can be used to convert first signal 1032 to a digital signal. Furthermore, in the case of a digital signal processor, a digital-to-analog converter can be used to convert a second signal 1042 to an analog signal. Sound amplification device 1020 can also comprise a receiver 1050. Receiver 1050 can be configured to receive second signal 1042 and generate a sound 1060.

According to an embodiment, audio system 1010 can be configured as a Behind-The-Ear (BTE) device. According to various embodiment, audio system 1010 may also comprise a Hearing Aid (HA), an Invisible-In-Canal (IIC) device, a Completely-In-Canal (CIC) device, an In-The-Canal (ITC) device, an In-The-Ear (ITE) device, a Receiver-In-Canal (RIC) device, Behind-The-Ear (BTE) device, an On-The-Ear (OTE) device, a Body-Worn (BW) device, a wireless device; a headset, earphones, a TDH series audiometric earphones device, an insert earphone device, an audiometric insert earphone device, an earbud, a speaker, a Bone-Anchored (BA) device, a Bone-Conduction (BC) device, a Personal Sound Amplification Product (PSAP) device, an audiometer, a telephone, a cell phone, a television, a radio, an audio system, a media player, a hearables device, a wearable audio device, a computer, a tablet, a laptop, a smart device and/or any other audio device and the like.

Figure 11:
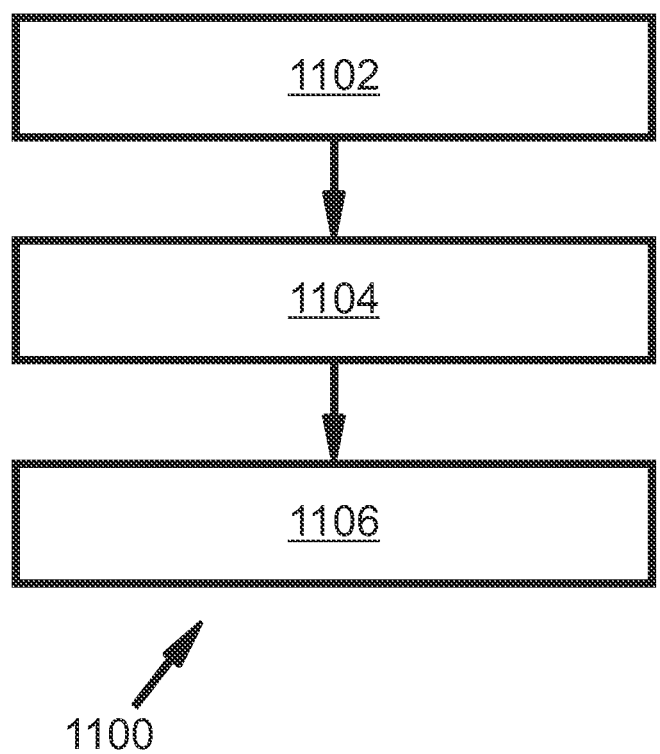
FIG. 11 illustrates a flow chart of a method for determining hearing ability.

FIG. 11 illustrates a method 1100 for determining the hearing ability of an individual. In step 1102, an audio system can generate a pulsating noise sound and present the pulsating noise sound to a user. A pulsating noise sound can be generated by a pulsating parametrically formulated noise generator similar to pulsating parametrically formulated noise generator 110 (see FIG. 1). According to an embodiment, the pulsating noise sound can be similar to diminishing pulsating noise sound 410 (see FIG. 4). The pulsating noise sound can comprise a pulsating parametrically formulated noise substantially within a first range or band of frequencies. According to an embodiment, the pulsating noise sound can pulsate at a rate of 4 pulses per second and can begin at a sound level of 85 dB HL (decibels Hearing Level) and diminish in volume over time at a rate of −0.5 dB per pulse. The pulsating noise sound can be presented to a user via a receiver, a headphone, a speaker, or any other sound output element or device.

In step 1104, the user can indicate via a user interface when the user perceives the pulsating noise sound to have disappeared or to have become imperceptible. According to various embodiments, a user interface can comprise one or more user inputs such as buttons, sliders, dials, sensors, external devices such as cell phones, and/or any other user interfaces or device.

In step 1106, the audio system can record the volume level of the pulsating noise sound at which the user indicated that the user had perceived the pulsating noise sound to have disappeared. This information can be stored as data on a data storage device included as part of the audio system.

According to an embodiment, method 1100 can be repeated using pulsating noise sounds comprised of different frequencies ranges or bands. Method 1100 can be practiced using a first ear of a user and subsequently repeated using the second ear of a user. According to an embodiment, an audio system may repeat an instance of method 1100 and compare the result to the result obtained in a previous instance of method 1100. According to an embodiment, if the result of the first instance of method 1100 and the result of the second instance of method 1100 using the same frequency band as used in the first instance differ by more than 3 dB, method 1100 can continue to be repeated until a difference of less than 3 dB is obtained. According to another embodiment, if the result of the first instance of method 1100 and the result of the second instance of method 1100 using the same frequency band as used in the first instance differ by more than 6 dB, method 1100 can be repeated until a difference of less than 6 dB is obtained.

According to an embodiment, method 1100 can be repeated for a plurality of frequency bands and for each ear as required. According to an embodiment, the volume of the pulsating noise sound can remain level at 85 dB HL for 1 second before diminishing in volume. According to various embodiments, many different variations, techniques and designs for method 1100 are possible and can be used to determine the hearing ability of an individual. These variations include, but are not limited to changes to instructions, user interfaces, user indicators, delays, initial volumes, pulsating rates, changes in volume per unit of time, criteria for authentication, calibrations, etc.

According to another embodiment, in step 1102, the pulsating noise sound can be similar to increasing pulsating noise sound 510 (see FIG. 5). The pulsating noise sound can comprise a pulsating parametrically formulated noise substantially within a first range or band of frequencies. According to an embodiment, the pulsating noise sound can pulsate at a rate of 5 pulses per second and can begin at a sound level of 0 dB HL (decibels Hearing Level) and increase in volume over time at a rate of +2 dB per pulse. According to an embodiment, in step 1104, the user can indicate via a user interface when the pulsating noise sound can be heard by the user or when the user perceives the pulsating noise sound to have appeared. According to an embodiment, in step 1106, an audio system can record the volume level of the pulsating noise sound at which the user indicated that the pulsating noise sound could be heard or at which the user had perceived the pulsating noise sound to have appeared. This information can be stored as data on a data storage device included as part of the audio system.

According to an embodiment, in step 1102, the volume of the pulsating noise sound can be absent for 1 second before the pulsating noise sound is first presented at 0 dB HL. According to various embodiments, many different variations, techniques and designs for method 1100 are possible and can be used to determine the hearing ability of an individual. According to an embodiment, several of the above described embodiments can be combined. As an example, according to an embodiment, method 1100 can be practiced using an increasing pulsating noise signal such as a noise sound 510 (see FIG. 5), and then subsequently repeated using a decreasing pulsating noise signal such as a noise sound 410 (see FIG. 4).

Figure 12:
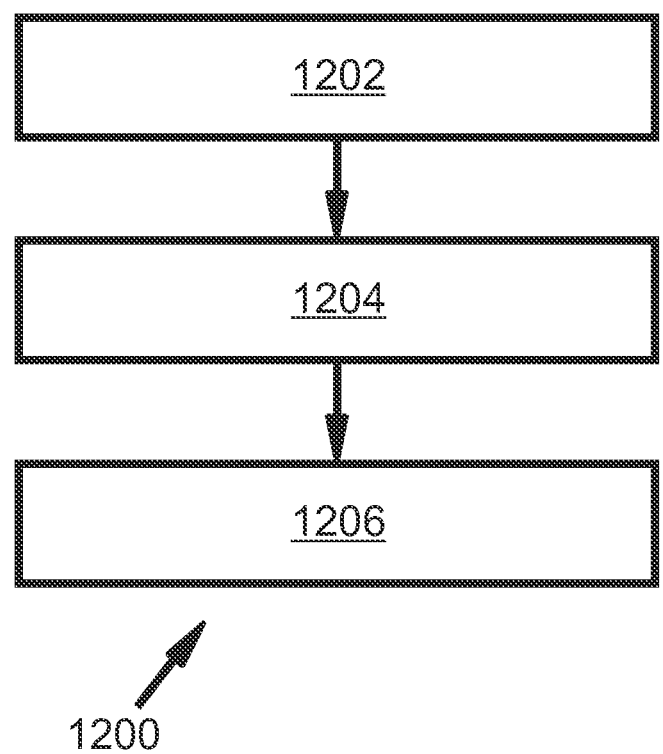
FIG. 12 illustrates a flow chart of a method for determining hearing ability.

FIG. 12 illustrates a method 1200 for determining the hearing ability of an individual. In step 1202, an audio system can generate a pulsating noise sound and present the pulsating noise sound to a user. A pulsating noise sound can be generated by a pulsating parametrically formulated noise generator similar to pulsating parametrically formulated noise generator 110 (see FIG. 1). According to an embodiment, the pulsating noise sound can be similar to an increasing pulsating noise sound 310 (see FIG. 3). The pulsating noise sound can comprise a pulsating parametrically formulated noise substantially within a first range or band of frequencies. According to an embodiment, the pulsating noise sound can pulsate at a rate of 4 pulses per second and can begin at a predetermined sound level or at a sound level which is determined by a user using a user interface. The pulsating noise sound can be presented to a user via a receiver, a headphone, a speaker, or any other sound output element or device. In step 1204, the user can adjust the sound level of the pulsating noise sound via a user interface and can adjust the user interface until the user perceives the pulsating noise sound to be barely audible or to have disappeared. According to various embodiments, a user interface can comprise one or more user inputs such as buttons, sliders, dials, sensors, external devices such as cell phones, and/or any other user interfaces or devices. The user can indicate that the pulsating noise sound has been substantially adjusted to be barely audible or to have disappeared using a user interface.

In step 1206, an audio system can record the volume level of the pulsating noise sound at which the user indicated that the user had perceived the pulsating noise sound to be barely audible or to have disappeared. This information can be stored as data on a data storage device included as part of the audio system.

Method 1200 can be repeated using pulsating noise sounds comprised of different frequencies ranges or bands. Method 1200 can be practiced using a first ear of a user and subsequently repeated using the second ear of a user. The audio system can repeat an instance of method 1200 and compare the result to the result obtained in a previous instance of method 1200. According to an embodiment, if the result of the first instance of method 1200 and the result of the second instance of method 1200 using the same frequency band as used in the first instance differ by more than 3 dB, method 1200 can be repeated until a difference of less than 3 dB is obtained. According to various embodiments, many different variations, techniques and designs for method 1200 are possible and can be used to determine the hearing ability of an individual. These variations include, but are not limited to changes to instructions, user interfaces, user indicators, delays, initial volumes, pulsating rates, changes in volume per unit of time, criteria for authentication, calibrations, etc.

Figure 13:
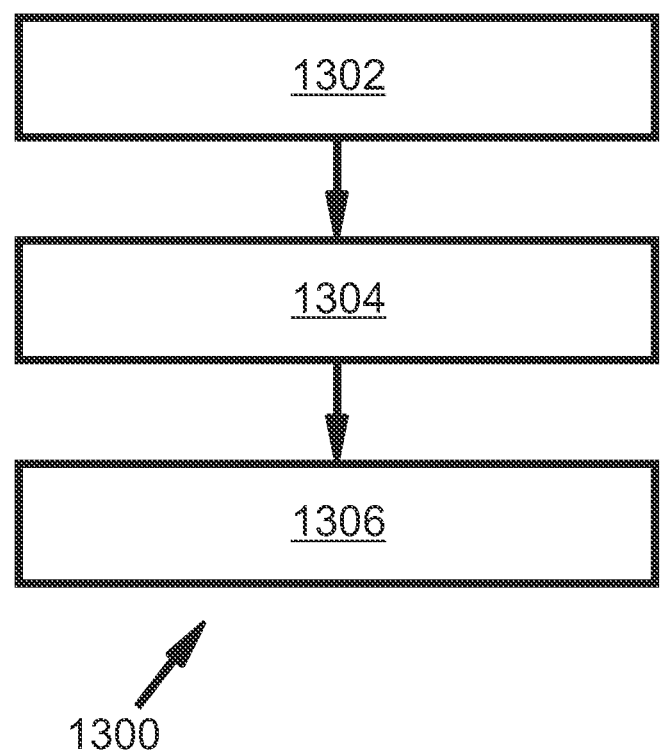
FIG. 13 illustrates a flow chart of a method for determining hearing ability; and, FIG. 14 illustrates a schematic diagram of an audio system.

FIG. 13 illustrates a method 1300 for determining the hearing ability of an individual. In step 1302, an audio system can generate a first pulsating noise sound and a second pulsating noise sound. According to an embodiment, the first pulsating noise sound can be similar to pulsating noise sound 610 (see FIG. 6) and the second pulsating noise sound can be similar to pulsating noise sound 612 (see FIG. 6). According to another embodiment, the first pulsating noise sound can be similar to pulsating noise sound 710 (see FIG. 7) and the second pulsating noise sound can be similar to pulsating noise sound 712 (see FIG. 7). According to another embodiment, the first pulsating noise sound and the second pulsating noise sound can be similar to noise sound 310 (see FIG. 3). The first and second pulsating noise sounds can be generated by one or more pulsating parametrically formulated noise generators similar to the pulsating parametrically formulated noise generator 110 (see FIG. 1). The audio system can present the first pulsating noise sound and second pulsating noise sounds to a user. The first pulsating noise sound can be presented to the first ear of a user and the second pulsating noise sound can be presented to the second ear of the user. The first and second pulsating noise sounds can comprise pulsating parametrically formulated noise substantially within a first range or band of frequencies. According to an embodiment, both of the first and second pulsating noise sound can pulsate at a rate of 4 pulses per second and can begin at a sound level which is above the threshold of hearing of the user, for example, 15 dB above the threshold of hearing of the user. The volume of the first and second pulsating noise sound can be adjusted by a user interface. According to various embodiments, a user interface can comprise one or more user inputs such as buttons, sliders, dials, sensors, external devices such as cell phones, and/or any other user interfaces or devices. The pulsating noise sound can be presented to a user via two receivers, headphones, speakers, or any other sound output elements or devices.

In step 1304, the user can adjust the relative sound level between the first and second pulsating noise sound via a user interface and can adjust the user interface until the user perceives the first and second pulsating noise sounds to be binaurally balanced or centered between both ears. According to an embodiment, the individual volumes of the first and second pulsating noise sounds can be independently controllable via a user interface, for example, the volume of the first pulsating noise sound can be increased while the volume of the second pulsating noise sound remains constant. According to another embodiment, the relative volume between the first and second pulsating noise sound can be adjustable via a user interface, for example, the volume of the first pulsating noise sound can be increased while the volume of second pulsating noise sound can be decreased in tandem. According to an embodiment, the user can indicate that the first and second pulsating noise sounds are perceived as binaurally balanced or centered between both ears using the user interface, for example by pressing a button. In step 1306, an audio system can record the volume level of the first and second pulsating noise sounds at which the user indicated that the user had perceived the first and second pulsating noise sound to be binaurally balanced or centered between both ears. This information can be stored as data on a data storage device included as part of the audio system.

According to an embodiment, method 1300 can be repeated using pulsating noise sounds comprised of different frequencies ranges or bands. According to an embodiment, an audio system can repeat an instance of method 1300 and compare the result to the result obtained in a previous instance of method 1300. According to an embodiment, if the result of the first instance of method 1300 and the result of the second instance of method 1300 using the same frequency band as used in the first instance differ by more than 3 dB, method 1300 can be repeated until a difference of less than 3 dB is obtained.

According to an embodiment, method 1300 can be repeated for each frequency band as required. According to various embodiments, many different variations, techniques and designs for method 1300 are possible and can be used to determine the hearing ability of an individual. These variations include, but are not limited to changes to instructions, user interfaces, user indicators, delays, initial volumes, pulsating rates, changes in volume per unit of time, changes in volume per movement or change in a user interface, criteria for authentication, calibrations, etc.

Figure 14:
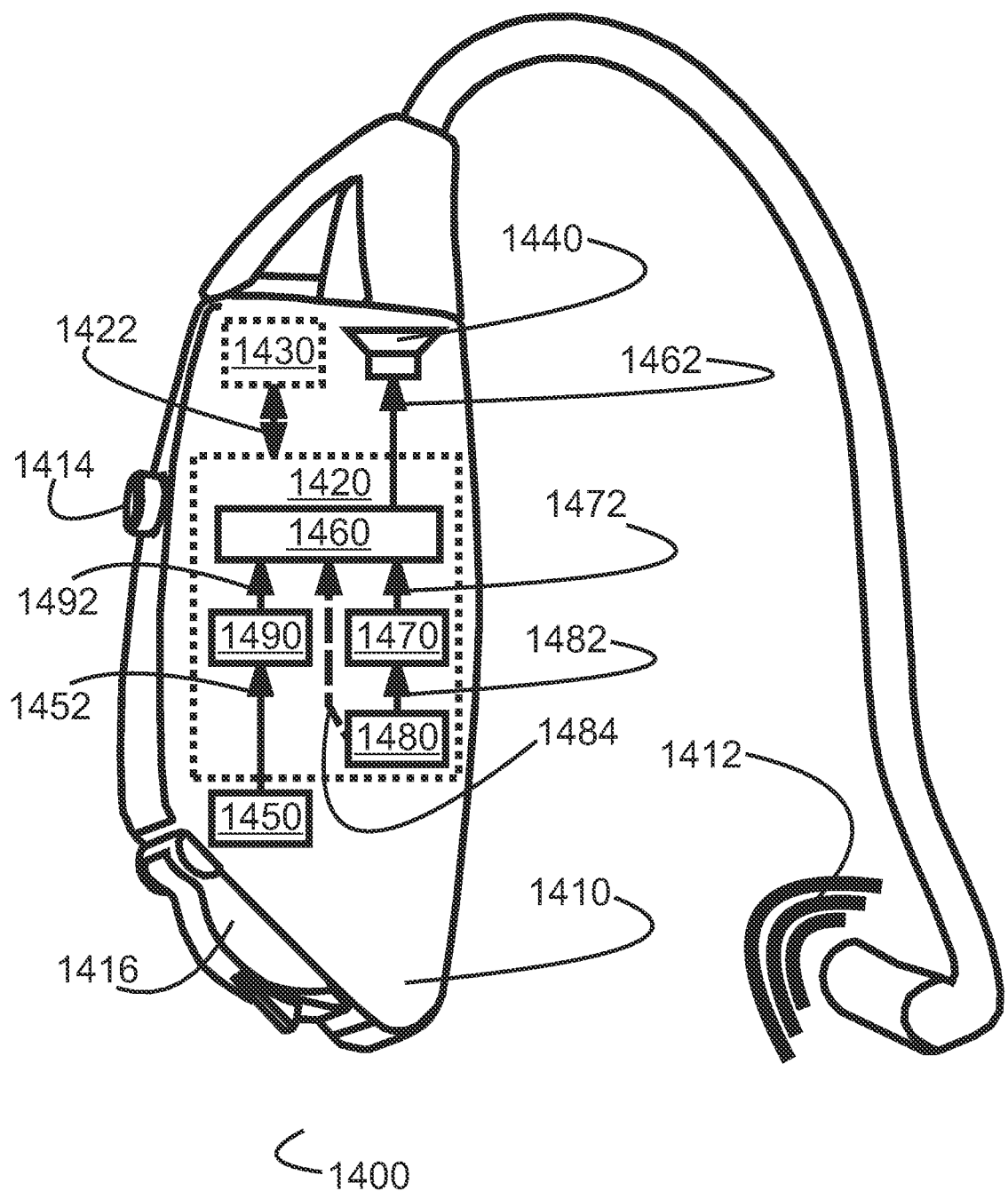

FIG. 14 illustrates a schematic diagram 1400 of an audio system 1410. Audio system 1410 comprises a microprocessor, microcontroller, or processor 1420. Processor 1420 can be used to perform multiple functions for audio system 1410 including administering hearing tests to a user of audio system 1410, generating test signals such as pulsating parametrically formulated noise signals, adjusting sound settings and prescriptive programming settings according to the user's individual responses to the hearing test, calculating parameters to generate a user specific treatment signal comprising parametrically formulated noise, generating a parametrically formulated noise treatment signal, receiving an audio signal from a microphone, sensor, or antenna, processing the audio signal and implementing noise reduction and signal amplification protocols according to the measured hearing ability of the user, mixing the processed audio signal with the treatment signal, outputting the mixed signal to a receiver or speaker. Processor 1420 is coupled to a memory device or storage device 1430. Storage device 1430 can store instructions to operate processor 1420 according to the various functions described above. Storage device can also store lookup tables and measured data from a user corresponding to the user's responses to the hearing test. Such tables and data can be used by processor to generate the treatment signal and process audio signals. Storage device 1430 can form part of the same system, chip, or device as processor 1420, as is the case with many microcontrollers, or storage device 1430 can be separate from processor 1420. In some embodiments, storage device 1430 may be located in a separate location from audio system 1410, for example, on a network storage device or a cloud storage configuration.

Processor 1420 comprises a parametrically formulated noise generator 1480. Parametrically formulated noise generator 1480 can generate a parametrically formulated noise test signal 1482 that can be received by a pulsating modulator 1470. Pulsating modulator 1470 can receive parametrically formulated noise test signal 1482 and modulate parametrically formulated noise test signal with a pulsating noise signal to generate a pulsating parametrically formulated noise test signal 1472. Pulsating parametrically formulated noise test signal 1472 can be received by a mixer 1460 or can be received directly by a speaker or receiver 1440. Receiver 1440 can generate sound 1412 which can be representative of the pulsating parametrically formulated noise test signal 1472 which can be presented to the user of audio system 1410 to test, measure, and determine the hearing ability of a user of audio system 1410. A user of audio system 1410 can respond to test sounds 1412 using a user interface 1414. Responses by the user can be recorded and stored as information or data within storage device 1430. Storage device 1430 can comprise any type of data storage device, including, for example, memory, volatile memory, non-volatile memory, RAM, flash, DRAM, SRAM, magnetic, EEPROM, etc. According to an embodiment, storage device 1430 can be remotely located from processor 1420 and can be accessed by processor 1420 via a wireless communication interface. Storage device 1430 can be accessed by processor 1420 as shown with bidirectional access 1422. Accordingly, processor 1420 can both read from and write to storage device 1430.

Parametrically formulated noise generator 1480 can also generate a parametrically formulated noise treatment signal 1484. Parametrically formulated noise treatment signal 1484 can comprise parametrically formulated noise that is contoured to the user's specific frequency dependent thresholds of hearing. The user's specific frequency dependent thresholds of hearing can be determined according to the data collected from the user's responses to the pulsating parametrically formulated noise tests. Parametrically formulated noise treatment signal 1484 can be received by mixer 1460 or can be received directly by receiver 1440. Receiver 1440 can generate sound 1412 which can be representative of the parametrically formulated noise treatment signal 1484 in isolation or mixed with a processed audio signal 1492.

Audio system 1410 can also comprise a microphone, sensor, or antenna 1450. Microphone 1450 can be used to receive sound input from a user's environment. Microphone 1452 can generate a second sound signal 1452. According to another embodiment, an antenna 1452 can receive a signal from an external source and pass the signal as second sound signal 1452 to signal processor 1490.

Signal processor 1490 can receive second sound signal 1452 and process second sound signal 1452 according to the amplification, attenuation, compression, frequency shifting, and/or noise filtering requirements of the user. Signal processor can generate a processed second sound signal 1492 which can be received by mixer 1460 and mixed with parametrically formulated noise treatment signal 1484 or can be received by receiver 1440, or another receiver incorporated into audio system 1410, directly. Mixer 1460 can receive one or more signals, such as processed second sound signal 1492 and parametrically formulated noise treatment signal 1484, and mix generate a third signal 1462. Third signal 1462 can be received by receiver 1440 which can generate sound 1412 representing third signal 1462.

According to an embodiment, audio system 1410 can be powered by a battery or power source 1416.

According to an embodiment, parametrically formulated noise signal 1482 can be generated utilizing storage device 1430 and processor 1420. Storage device 1430 can store, for example, a first series of values corresponding to the amplitude of a first periodic wave having a first frequency sampled according to a first sampling rate over a first period of time. Additionally, the storage device 1430 can store, for example, a second series of values corresponding to the amplitude of a second periodic wave having a second frequency sampled according to the first sampling rate over a second period of time. According to an embodiment, a storage device 1430 can store plurality of series of values corresponding to the amplitude of a plurality of periodic waves having a plurality of different frequencies and sampled according to various sampling rates over various periods of time. According to an embodiment, processor 1420 can be coupled to the memory device 1430 and configured to recursively make a random or pseudorandom selection between, for example, the first periodic wave and the second periodic wave and output a parametrically formulated noise signal 1482 comprising the series of values corresponding to each recursively selected periodic signal. According to an embodiment, such a parametrically formulated noise signal 1482 can have a power spectrum that has a generally or substantially uniform amplitude between the first frequency and the second frequency. Furthermore, processor 1420 can be configured to modify the amplitude of the parametrically formulated noise signal 1482, via pulsating modulator 1470, using a third series of values stored on the storage device 1430 which can correspond to levels for amplitude modification so as to modulate the parametrically formulated noise signal and create a pulsing amplitude with alternating periods of greater amplitude and diminished amplitude. The processor can then output such a pulsating parametrically formulated noise signal 1472.

Audio system 1410 is shown in FIG. 14 in the form of a hearing aid, however, according to various embodiments, elements or components of audio system, such as processor 1420, storage device 1430, receiver or speaker 1440, and microphone or antenna 1450, user interface 1414, and other elements shown in FIG. 14, can be incorporated into any audio system. For example, the aforementioned elements, components and combinations thereof can be incorporated into a computer, cell phone, telephone, tablet, television, hearable device, radio, stereo, etc.

In reference to all of the foregoing disclosure, the above described embodiments enable solutions, improvements, and benefits to many problems and issues affecting conventional audio systems and conventional audio devices and offer improved functionality for audio systems and audio devices.

As disclosed herein, an audio system can generate a test signal comprising pulsating parametrically formulated noise. Such test signals can be used by the audio system to test, measure and determine the hearing ability of a user of the audio system. The audio system can generate a treatment signal comprising parametrically formulated noise that is contoured to the user's specific frequency dependent thresholds of hearing. Such treatment signals can be effective in improving the hearing ability of a user of the audio system who may have sensorineural hearing loss. Such treatment signals can provide an alternative or supplement to sound-amplification for the mitigation of the effects of sensorineural hearing loss.

Parametrically formulated noise can be a purposefully designed and engineered sound signal. As disclosed herein, a parametrically formulated noise generator can be precisely programmed to provide parametrically formulated noise contoured to an individual's specific frequency dependent thresholds of hearing. The power spectrum of the contoured parametrically formulated noise can be substantially invariant during even short phoneme intervals (e.g. less than 50 milliseconds) and can allow any additional energy from any speech phoneme to "activate" and trigger a sensorineural hearing response. Parametrically formulated noise can add to speech and the other signals received by the cochlea so that the cochlea can be activated by faint sound levels and respond faithfully to narrow frequency ranges.

According to an embodiment, a single system or device can be used to both test the hearing ability of an individual and provide parametrically formulated noise contoured to an individual's specific frequency dependent thresholds as a treatment signal. Accordingly, this embodiment avoids any changes in acoustic configuration which would require calibration and further programming modifications.

According to an embodiment, parametrically formulated noise can be delivered to the ear canal through a thin tube (0.8 mm inner diameter) from a Behind-The-Ear (BTE) device. Accordingly, the ear canal would be minimally occluded. This embodiment can maximize the natural amplification occurring with the pinna effect and ear canal resonance.

According to an embodiment, the length of a thin tube could first be adjusted to the individual's ear geometry as the length of the thin tube can directly affect its acoustic impedance. Additionally, an individual's hearing ability could be determined after the length of the thin tube had been adjusted.

According to an embodiment, an individual with hearing loss is able to self-test hearing ability using the device and reprogram the device to compensate for changing hearing loss, to compensate for changing receiver (speaker) sensitivity over time, to compensate for changing microphone sensitivity over time, or to compensate for the individual's own perception and response errors during testing.

As disclosed herein, a system can be configured where a hearing testing signal and a hearing treatment signal are both comprised of parametrically formulated noise. The treatment signal can have little or no calibration error given that it is also comprised of parametrically formulated noise.

According to an embodiment, an individual can repeatedly self-test until satisfaction is achieved.

In view of the above it is evident that a pulsating parametrically formulated noise signal can be generated by an audio device in order to determine the hearing ability of an individual. Furthermore, the same audio device can be used to generate a parametrically formulated noise signal which is beneficial in increasing the hearing ability of the individual.

Benefits, other advantages, and solutions to problems and issues have been described above with regard to particular embodiments. Any benefit, advantage, solution to problem, or any element that may cause any particular benefit, advantage, or solution to occur or to become more pronounced are not to be construed as required or necesarry features or components of any or all the claims.

In view of all of the above, it is evident that novel audio systems, audio devices, noise signals, noise generators, and methods are disclosed. Included, among other embodiments, is an audio system which can both determine the hearing ability and increase the hearing ability of an individual by using parametrically formulated noise. Improved speech intelligibility can be obtained, according to an embodiment, by mixing parametrically formulated noise with an audio or speech signal. Parametrically formulated noise can be configured to have a power spectrum amplitude that is a function of frequency across as range of frequencies. Furthermore, parametrically formulated noise can have a power spectrum amplitude that is a function of a user's hearing threshold across a range of frequencies as measured using pulsating parametrically formulated noise. According to an embodiment, characteristics of the power spectrum amplitude of a pulsating parametrically formulated noise across a range of frequencies can be controlled or shaped according to a selection of parameters representative or controlling of a ratio of duration of the various periodic waves used to construct the parametrically formulated noise.

While the subject matter of the invention is described with specific and example embodiments, the foregoing drawings and descriptions thereof depict only typical embodiments of the subject matter, and are not therefore to be considered limiting of its scope. It is evident that many alternatives and variations will be apparent to those skilled in the art and that those alternatives and variations are intended to be included within the scope of the present invention. For example, some embodiments described herein include some elements or features but not other elements or features included in other embodiments, thus, combinations of features or elements of different embodiments are meant to be within the scope of the invention and are meant to form different embodiments as would be understood by those skilled in the art. Furthermore, any of the above-described elements, components, blocks, systems, structures, devices, filters, noise generation methods, ranges and selection of ranges, applications, programming, signal processing, signal analysis, signal filtering, implementations, proportions, flows, or arrangements, used in the practice of the present invention, including those not specifically recited, may be varied or otherwise particularly adapted to specific environments, users, groups of users, populations, manufacturing specifications, design parameters, or other operating requirements without departing from the scope of the present invention. Additionally, the steps recited in any method or processing scheme described above or in the claims may be executed in any order and are not limited to the specific order presented in the above description or in the claims. Finally, the components and/or elements recited in any apparatus claims may be assembled or otherwise operationally configured in a variety of permutations and are accordingly not limited to the specific configuration recited in the claims.

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of the invention.

What is claimed is:

1. An audio system, comprising:
    a parametrically formulated noise generator, wherein the parametrically formulated noise generator is configured to generate a parametrically formulated noise test signal substantially within a first range of frequencies and a parametrically formulated noise treatment signal, wherein the parametrically formulated treatment signal is a function of the user's frequency dependent thresholds of hearing;
    a pulsating modulator, wherein the pulsating modulator is configured to receive the parametrically formulated noise test signal and generate a pulsating noise test signal;
    a receiver, wherein the receiver is configured to receive the pulsating noise test signal and generate a pulsating test sound to a user; and,
    a user interface, wherein the user interface is configured to allow a user to indicate to the audio system when a first test event has occurred relating to the pulsating test sound and wherein the user's indication of the occurrence of a test event corresponds to a measure of the user's frequency dependent thresholds of hearing.

2. The audio system of claim 1, wherein the pulsating noise test signal is configured to decrease in amplitude over time.

3. The audio system of claim 2, wherein the first test event comprises the user's perceived absence of the pulsating test sound.

* * * * *